United States Patent
Case, Jr.

(10) Patent No.: US 8,028,443 B2
(45) Date of Patent: Oct. 4, 2011

(54) SYSTEMS FOR ACTIVATING AND/OR AUTHENTICATING ELECTRONIC DEVICES FOR OPERATION WITH FOOTWEAR

(75) Inventor: Charles Whipple Case, Jr., Lake Oswego, OR (US)

(73) Assignee: NIKE, Inc., Beaverton, OR (US)

(*) Notice: Subject to any disclaimer, the term of this patent is extended or adjusted under 35 U.S.C. 154(b) by 1864 days.

(21) Appl. No.: 11/166,351

(22) Filed: Jun. 27, 2005

(65) Prior Publication Data
US 2007/0011919 A1    Jan. 18, 2007

(51) Int. Cl.
*A43B 5/00*    (2006.01)
*A43B 23/00*    (2006.01)

(52) U.S. Cl. ............................................. 36/132; 36/137

(58) Field of Classification Search .................... 36/132, 36/137, 139, 136; 362/103, 802
See application file for complete search history.

(56) References Cited

U.S. PATENT DOCUMENTS

| | | | | |
|---|---|---|---|---|
| 4,350,853 | A | * | 9/1982 | Ganyard ..................... 200/52 R |
| 5,335,188 | A | | 8/1994 | Brisson |
| 5,422,628 | A | * | 6/1995 | Rodgers ..................... 340/573.1 |
| 5,596,652 | A | | 1/1997 | Piatek et al. |
| 5,598,849 | A | | 2/1997 | Browne |
| 5,692,324 | A | * | 12/1997 | Goldston et al. ................. 36/137 |
| 5,724,265 | A | | 3/1998 | Hutchings |
| 5,793,882 | A | | 8/1998 | Piatek et al. |
| 5,890,997 | A | | 4/1999 | Roth |
| 5,931,763 | A | | 8/1999 | Alessandri |
| 5,955,667 | A | | 9/1999 | Fyfe |
| 6,000,149 | A | | 12/1999 | Pomerantz |
| 6,012,822 | A | * | 1/2000 | Robinson ..................... 362/103 |
| 6,013,007 | A | | 1/2000 | Root et al. |
| 6,018,705 | A | | 1/2000 | Gaudet et al. |
| 6,030,089 | A | * | 2/2000 | Parker et al. .................. 362/103 |
| 6,052,654 | A | | 4/2000 | Gaudet et al. |
| 6,077,193 | A | | 6/2000 | Buhler et al. |
| 6,375,612 | B1 | | 4/2002 | Guichon et al. |
| 6,396,413 | B2 | | 5/2002 | Hines et al. |
| 6,424,264 | B1 | | 7/2002 | Giraldin et al. |
| 6,430,843 | B1 | | 8/2002 | Potter et al. |
| 6,526,158 | B1 | | 2/2003 | Goldberg |

(Continued)

FOREIGN PATENT DOCUMENTS

EP    0 589 607 A1    9/1993
(Continued)

OTHER PUBLICATIONS

Partial International Search Report dated Jan. 12, 2007.
(Continued)

*Primary Examiner* — Ted Kavanaugh
(74) *Attorney, Agent, or Firm* — Banner & Witcoff Ltd.

(57) ABSTRACT

Articles of footwear and footwear systems include modules, e.g., for sensing physical and/or physiological characteristics associated with use of the footwear or for performing other functions. Such systems and methods may use physical or other interaction(s) between the module and the article of footwear for activating and/or deactivating the module and/or sensing devices included with the module, for confirming whether the module and footwear are authorized for use with one another, and/or for automatic data algorithm selection methods. Additionally, such systems and methods also may use the activation and/or authentication systems for the module for data input to the module. Some examples of such systems and methods may utilize magnets and magnetic sensing systems and/or light (or other radiation) sources and sensing systems for activation, authentication, data input, and/or algorithm selection.

31 Claims, 11 Drawing Sheets

U.S. PATENT DOCUMENTS

| | | |
|---|---|---|
| 6,531,963 B1 | 3/2003 | Nyfelt |
| 6,569,092 B1 | 5/2003 | Guichon et al. |
| 6,600,407 B2 | 7/2003 | Paek |
| 6,614,392 B2 | 9/2003 | Howard |
| 6,788,200 B1 * | 9/2004 | Jamel et al. .............. 340/539.13 |
| 6,865,825 B2 | 3/2005 | Bailey, Sr. et al. |
| 6,876,947 B1 | 4/2005 | Darley et al. |
| 6,882,955 B1 | 4/2005 | Ohlenbusch et al. |
| 7,219,449 B1 * | 5/2007 | Hoffberg et al. .................. 36/88 |
| 2001/0054014 A1 | 12/2001 | Noda et al. |
| 2002/0022551 A1 | 2/2002 | Watterson et al. |
| 2002/0077883 A1 | 6/2002 | Lancos et al. |
| 2002/0080198 A1 | 6/2002 | Giraldin et al. |
| 2002/0091796 A1 | 7/2002 | Higginson et al. |
| 2002/0142887 A1 | 10/2002 | O'Malley |
| 2002/0147629 A1 | 10/2002 | Alsafadi et al. |
| 2002/0147642 A1 | 10/2002 | Avallone et al. |
| 2002/0156677 A1 | 10/2002 | Peters et al. |
| 2002/0165758 A1 | 11/2002 | Hind et al. |
| 2002/0173407 A1 | 11/2002 | Bowman |
| 2002/0174025 A1 | 11/2002 | Hind et al. |
| 2003/0009308 A1 | 1/2003 | Kirtley |
| 2003/0009382 A1 | 1/2003 | D'Arbeloff et al. |
| 2003/0009913 A1 | 1/2003 | Potter et al. |
| 2003/0040922 A1 | 2/2003 | Bodin |
| 2003/0090386 A1 | 5/2003 | Giraldin et al. |
| 2003/0160732 A1 | 8/2003 | Van Heerden et al. |
| 2003/0163287 A1 | 8/2003 | Vock et al. |
| 2004/0177531 A1 | 9/2004 | DiBenedetto et al. |
| 2009/0313857 A1 * | 12/2009 | Carnes et al. ................... 36/132 |

FOREIGN PATENT DOCUMENTS

| | | |
|---|---|---|
| EP | 0589607 A | 3/1994 |
| EP | 1 552 761 A1 | 7/2005 |
| EP | 1552761 A | 7/2005 |
| JP | 05-161724 | 6/1993 |
| JP | 10127302 | 5/1998 |
| JP | 10127302 A | 5/1998 |
| JP | 2001-155121 | 6/2001 |
| JP | 2004-313407 | 11/2004 |

OTHER PUBLICATIONS

International Search Report dated Apr. 17, 2007.
First Office Action issued in corresponding Chinese Patent Application, Application No. 2006800276439, issued Oct. 9, 2009.
Translation of Japanese Patent Application No. 2008-519332 Notice of Reasons for Rejection dated Jan. 12, 2011.

* cited by examiner

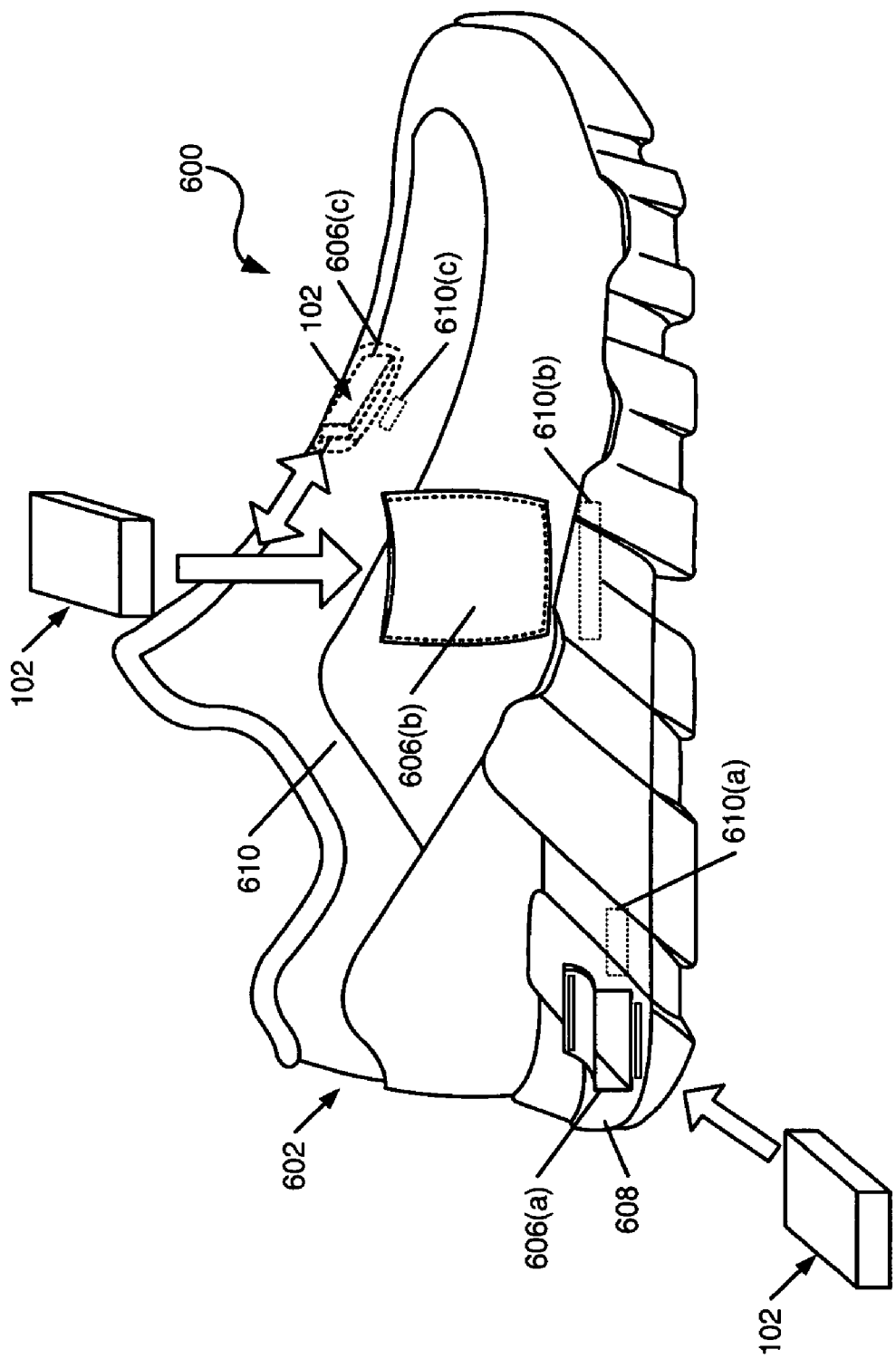

SYSTEMS FOR ACTIVATING AND/OR AUTHENTICATING ELECTRONIC DEVICES FOR OPERATION WITH FOOTWEAR

FIELD OF THE INVENTION

This invention relates generally to footwear and footwear systems that include one or more electronic modules. At least some example aspects of this invention utilize physical and/or other interactions between the module and the article of footwear to which it is attached (and/or an absence of such interactions) for providing module activation/authentication information and/or data processing algorithm selection information (e.g., interactions between magnet sources or light sources with appropriate sensors). Additional example aspects of the invention involve data input systems for footwear modules.

BACKGROUND

Footwear technology has evolved in recent years such that at least some examples of modern footwear, such as athletic footwear, may include various electronic components. For example, footwear systems are known that include devices for sensing and controlling the degree of impact force attenuation provided by the article of footwear, based, for example, on characteristics of the active use of the footwear. Other electronic systems and features associated with footwear are also known.

SUMMARY

Aspects of this invention relate to articles of footwear and/or footwear systems that include one or more electronic modules. These electronic modules may include electronic devices for performing various functions, such as electronic modules and devices for providing RFID information or activating RFID systems, electronic modules and devices for measuring, sensing, receiving, and/or transmitting data or information, such as data or information relating to various physical and/or physiological characteristics associated with use of the footwear, data or information relating to the physical exertion that takes place while wearing footwear equipped with the module, identifying data or information, and/or the like. Aspects of the invention relate to various systems and methods for activating and/or deactivating the module and/or electronic devices (e.g., sensing devices, transmission devices, receiving devices, etc.) included with or controlled by the module. Additional aspects of the invention relate to various systems and methods for confirming whether the module and an article of footwear are authorized for use with one another, systems and methods for data input to the module, and/or systems and methods for automatic data algorithm selection for use by the module. In at least some examples of this invention, physical or other interactions between the module and the article of footwear with which it is engaged (and/or an absence of such interactions) may be used for activating and/or deactivating the module and/or electronic devices included with the module, for confirming whether the module and footwear are authorized for use with one another, and/or for automatic data algorithm selection. Systems and methods according to at least some more specific examples of this invention utilize light sources and detectors and/or magnets and magnetic sensing systems, such as Hall sensor systems, to activate the various systems (e.g., the module or electronic devices included with the module) and/or to initiate various methods, optionally without the need for further independent user input. At least some examples of the invention utilize magnetic or light interactions between the module and the article of footwear and/or changes in the interaction when the module and article of footwear are engaged such that no physical element actually crosses the border of or enters into the module to cause the interaction or the change in interaction. This feature allows the module to be constructed in a tough, waterproof, and/or durable manner.

BRIEF DESCRIPTION OF THE DRAWINGS

A more complete understanding of the present invention and at least some features and advantages thereof may be acquired by referring to the following description and the accompanying drawings, in which like reference numbers indicate like features throughout, and wherein:

FIG. 6 illustrates examples of module activation/authentication features, module securing element location determination features, and/or data algorithm selection features that may be used in accordance with some examples of this invention;

DETAILED DESCRIPTION

In the following description of various examples of the present invention, reference is made to the accompanying drawings, which form a part hereof, and in which are shown by way of illustration various structures, embodiments, and examples in which aspects of the invention may be practiced. It is to be understood that other embodiments may be utilized and structural and functional modifications may be made without departing from the scope of the present invention.

I. General Description Of Aspects Of The Invention

Figure 1:
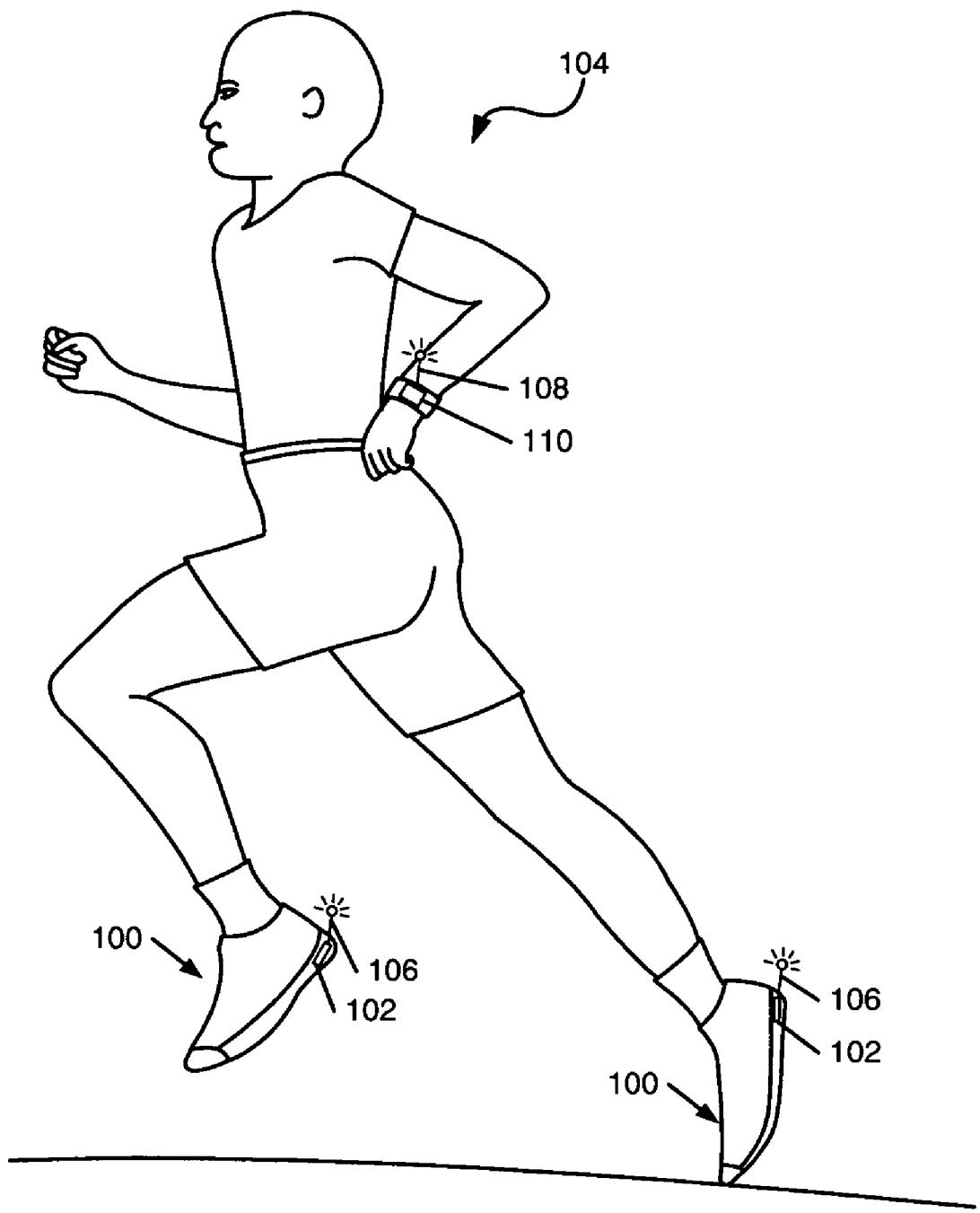
FIG. 1 illustrates an example environment in which footwear, footwear systems, measuring modules, and methods in accordance with examples of this invention may be used.

Aspects of the present invention relate generally to footwear. As shown in FIG. 1, which generally illustrates an example of the invention and an example environment in which it may be used, one or more individual articles of footwear 100 (such as athletic footwear) may be equipped with electronic modules, such as performance measuring modules 102, other measuring modules 102, or modules 102 for other purposes (e.g., data transmission, reception, RFID, radio or other audio/video transmission/reception, etc.). The modules 102 may include electronic devices for sensing or collecting information during a performance (e.g., during an athletic event or exercise or other performance), for providing information to the footwear user or others (e.g., transmission devices, RFID devices, etc.), and/or for controlling another device (e.g., a footwear impact attenuation system, etc.). While any desired or suitable type(s) of information may be sensed, provided to the user or others, and/or otherwise used or generated, more specific examples of the types of information include: user traveling speed information; distance traveled information; GPS information; altitude information; user physiological information; information derived from the GPS, speed, distance, physiological, or other information (e.g., warning information, route information, geographical information, etc.); RFID generated information; and the like. Additionally or alternatively, the module 102 may be used to control other devices or functions and/or to provide data to other devices, including devices present as part of the article of footwear, on the user's person, carried by the user, or at other locations, such as active impact-attenuation elements, display devices, data receiving devices, etc.

As shown in the example of FIG. 1, as the user 104 moves, devices provided in the modules 102 mounted to or included in the footwear 100 will measure one or more physical or physiological characteristics associated with the motion and/or with the use of the footwear (e.g., like speed and distance information, GPS information, pulse rate, heart rate, and/or the type(s) of information described above), or perform other desired functions. If desired, the data may be stored in a memory (e.g., a memory included with the module 102, provided in the footwear 100, provided with a peripheral device, etc.), e.g., for later use and/or analysis, and/or it may be transmitted to the user or others, e.g., via wireless transmission devices 106 optionally included as part of the module 102 or the article of footwear 100. Optionally, if desired, the module 102 and/or the footwear 100 may include one or more microprocessors or other data processing capability to enable processing of the collected data before transmitting the data or other information to the user 104 or others.

The data or desired information may be conveyed to the user 104 or others in any desired manner without departing from the invention, for example, to a wireless receiver 108 provided with a display device 110. Optionally, if desired, the display device 110 may be equipped with a microprocessor to enable initial processing of the raw data sent by the module 102 or footwear 100, to enable further processing of data and/or information sent by the module 102 or footwear 100, etc. As more specific examples, the display device 110 may include various electronic devices, such as portable, user carried devices, e.g., a watch, a PDA type device, a cellular telephone, an MP3 or other audio player, a head worn display device, a pager type device, headphones or earphones, etc. Any type of "display device" also may be provided, such as audio devices, video devices, audio/video devices, alphanumeric displays, etc.

In light of this general example and general description of an example environment of use, various example aspects of the invention will be described in more detail below, including various example features relating to: the manner in which the module may be engaged with a footwear structure, the manner in which the module and/or electronic devices included with it may be activated, the manner in which use of the module by a specific user or in a specific article of footwear may be authenticated, the manner in which data processing algorithms may be selected, the manner in which input data may be entered, and/or the like.

A. Automatic ON/OFF

One aspect of this invention relates to footwear systems including electronic devices, such as devices that provide information to the footwear wearer or others, such as physical or physiological information associated with use of the article of footwear and/or associated with the wearer's performance while wearing the article of footwear. In accordance with at least some examples of this invention, a footwear system may include: (a) an article of footwear having a module securing element; (b) a module removably engaged with the module securing element, wherein the module includes an electronic device (e.g., a sensing element that senses at least one physical or physiological characteristic associated with use of the article of footwear (e.g., speed and/or distance information, jump height information, GPS information, altitude information, user physical or physiological information, midsole compression information, gaming information, etc.)); and (c) an activation system that senses whether the module is engaged with the module securing element and activates the module or at least a first function of the module (e.g., the electronic device or some portion or function thereof, etc.) when the module is determined to be engaged with the module securing element. If desired, at least a first portion of the activation system may be included with and/or as part of the article of footwear, and a second portion of the activation system may be included with and/or as part of the module. The first portion of the activation system may be provided in or on the article of footwear in a position such that it is located proximate to the module securing element at least when the article of footwear is in use.

In at least some examples of the invention, the module, or at least some functions of the module, may be initiated or enabled automatically, for example, whenever the module is engaged at the module securing element and/or whenever the module is detected as being located at the module securing element. Determination as to whether the module is located at the module securing element and/or detection of the module at the module securing element may take place in any suitable or desired manner without departing from the invention. For example, the activation system may include a magnetic sensor system, a piezoelectric system, an accelerometer, a light sensor, or the like that produces an output when the module is included at or engaged with the module securing element. When the activation system includes a magnetic sensor, such as a Hall sensor system, a first portion of the magnetic sensor system (e.g., a magnet, a magnetic sensor, etc.) may be included with the article of footwear, and a second portion of the magnetic sensor system (e.g., a magnetic sensor, a magnet, etc.) may be included with the module. In other examples, if desired, either of the module or the article of footwear may include both the source and the sensor, but changes in the sensed magnetic characteristics may be sensed when the module is engaged with the module securing element. In at least some examples of such systems, if the article of footwear and the module do not each include the corresponding parts of the activation system and/or do not induce a predetermined change in the sensed characteristic, the module will not be activated and/or will be disabled and/or various functions of the module will not be activated and/or will be disabled. Examples of activation of the module and/or functions of the module will be described in more detail below in connection with various figures.

The module may be secured to the article of footwear in any desired manner without departing from this invention, e.g., the module securing element may take on any desired form without departing from the invention. In at least some examples of this invention, the module will be releasably secured to the article of footwear, e.g., such that it can be readily removed therefrom, if desired. As some more specific examples, the module securing element may take the form of a pocket, groove, or slot, formed in or on the footwear upper member or sole member, into which the module may be received. The module also may be held to the article of footwear in any desired manner without departing from the invention, such as via mechanical connectors, such as straps, flaps, hook-and-loop type fasteners, snaps, hooks, other mechanical fasteners, retaining walls or elements, tension fittings, detents, spring loading, etc.

In at least some examples of the invention, the module, or at least some functions of the module, may be initiated or enabled automatically, for example, whenever the module is engaged at the module securing element and/or whenever the module is detected at the module securing element. In accordance with other aspects of the invention, however, activation of the module and/or various functions of the module may be somewhat more selective. Another example aspect of this invention relates to a footwear system that includes: (a) an article of footwear having a module securing element; (b) a module removably engaged with the module securing element, wherein the module includes an electronic device (e.g., a sensing element that senses at least one physical or physiological characteristic associated with use of the article of footwear); and (c) an activation system that senses whether the module is engaged with the module securing element in a first orientation and activates the module or at least a first function of the module (e.g., the electronic device or some portion or function of the electronic device, etc.) when the module is engaged with the module securing element in the first orientation. In at least some examples of such systems, if the module is engaged with the module securing element in a manner other than in the first orientation (e.g., other than in a predetermined activation orientation), the module may be shut off, deactivated, disabled, not turned on, and/or not activated and/or various functions of the module may be shut off, deactivated, disabled, not turned on, and/or not activated.

These example features of the invention may be used to switch the module and/or various functions of the module on and off. As some more specific examples, when the module is engaged with the module securing element in the first orientation, this will turn the module on and/or activate various functions of the module. Removing the module from the module securing element, flipping it over, rotating it, and/or the like, and then re-engaging it with the module securing element may be detected, e.g., by a magnetic sensor or other detector systems as described above, and these changes will place the module at an orientation other then the predetermined activation orientation. In response to these orientation changes (and/or whenever the module is engaged with a module securing element in an orientation other then the predetermined activation orientation), the module may be shut off and/or various functions of the module may be shut off, disabled, etc. This feature may be used to extend battery life; shut down module transmission/reception capabilities (if any) for airline travel, hospital use, and/or use at other transmission/reception sensitive localities; etc. In at least some examples of such systems, if the article of footwear and the module do not each include the corresponding parts of the activation system and/or do not otherwise induce an expected interaction and/or change in interaction, the module will not be activated and/or will be disabled and/or various functions of the module will not be activated and/or will be disabled.

As described above, various portions of the activation system may be included with the article of footwear and/or the module, and the various types of activation systems, sensor systems, securing elements, securing methods, etc. as described above may be used without departing from this aspect of the invention. Also, various arrangements of the portions of the footwear system (e.g., the module, activation system, sensing elements, etc.), for example, as described above, may be used without departing from this aspect of the invention.

Additional aspects of the invention relate to methods of activating an electronic module, e.g., for collecting physical or physiological data, e.g., during exercise, workouts, athletic performances, etc. Such methods may include, for example: (a) engaging an electronic module with a module securing element provided in or on an article of footwear (e.g., optionally in a readily releasable manner), wherein the module includes an electronic device (e.g., a sensing element that senses at least one physical or physiological characteristic associated with use of the article of footwear); and (b) automatically activating the module or at least a first function of the module in response to the engaging. Optionally, as part of the activation procedure, activation will occur if and only if the module is oriented with respect to the module securing element in a predetermined activation orientation.

In such methods, as described above, an activation system may be associated with at least one of the module and/or the article of footwear, and this activation system may sense when the module is engaged at the module securing element and/or whether the module is oriented at the predetermined activation oriented. The module may be turned on and/or activated and/or various functions of the module may be turned on and/or activated when the module is engaged with the module securing element (optionally in the proper activation orientation). If the module is not engaged with the module securing element, if it is removed from the module securing element, and/or if it is oriented in a manner other than the predetermined activation orientation, the module may be turned off or deactivated and/or various functions of the module may be turned off or deactivated (optionally after a predetermined time period has elapsed).

In methods according to examples of the invention, the various portions of the activation system may be included with the article of footwear and/or with the module, and the various types of activation systems, sensor systems, securing elements, securing methods, etc. as described above may be used. Also, various arrangements of the elements (e.g., the module, activation system, sensing elements, etc.), like those described above, may be used for practicing these example method aspects in accordance with the invention. Also, if desired, reorienting the module with respect to the module securing element (e.g., flipping it over, rotating it, etc.) may be used to turn off or deactivate the module and/or various functions of the module, in accordance with at least some example methods of the invention.

B. Authentication Features

Additional aspects of this invention relate to footwear systems that include some type of authentication system before a module associated therewith will operate. Such footwear systems may include, for example: (a) an article of footwear having a module securing element; (b) a module removably engaged with the module securing element, wherein the module includes an electronic device (e.g., a sensing element that senses at least one physical or physiological characteristic associated with use of the article of footwear); and (c) an authentication system that determines whether the article of footwear and the module are authorized for operation with one another. Once activated, the electronic device may perform any desired function, such as radio or other audio/video communication functions, data transmission and/or reception functions, physical and/or physiological performance measuring and/or monitoring functions (e.g., speed and/or distance sensing, jump height sensing, etc.), GPS information providing functions, altitude measuring functions, midsole compression sensing functions, RFID or other data transmission and/or reception functions, etc.

Any type of authentication system may be used without departing from the invention. For example, in at least some examples of this aspect of the invention, a first portion of the authentication system may be included with the article of footwear and a second portion of the authentication system may be included with the module. As some even more specific examples, at least some of the systems described in the section above may be considered as providing a basic authentication system. For example, as described above, some example systems may require the module to be oriented in a predetermined manner with respect to the module securing element before the module will operate and/or before it will provide the desired data. In other examples, the module and the article of footwear both must contain a portion of the activation system and/or otherwise cause a predetermined interaction or change in a sensed condition before the module and/or at least some of its functions are activated. Therefore, in these examples, the module will not work with any type of shoe, but only with shoes that include at least a portion of the required activation (or authentication) system and/or only with shoes that will cause a predetermined interaction and/or change in a sensed interaction or parameter.

Various types of systems may be used for authentication without departing from the invention, such as magnetic sensor systems, piezoelectric sensor systems, accelerometers, light (or other radiation) sensor systems, and the like. As more specific examples, a first portion of a light or magnetic sensor system (e.g., a magnet, a magnetic sensor, a light source, a light detector, etc.) may be included with the article of footwear and a second portion of the sensor system (e.g., a magnetic sensor, a magnet, a light sensor, a light source, etc.) may be included with the module, and a specific orientation between these elements may be required before the module will be turned on, activated, and/or enabled for use. As additional examples, magnetic pole orientation, magnetic field strength at the magnetic sensor (e.g., at least a threshold strength, strength within a predetermined range, etc.), magnetic field direction at the magnetic sensor, detected light wavelength, detected light pattern, detected light direction, detected light intensity, and the like may be used as part of the information necessary to authenticate the module/footwear combination (e.g., to determine whether the article of footwear and the module are authorized for operation with one another). As additional examples, the article of footwear or the module may include multiple magnets or light sources, and overall magnetic pole orientation information, magnet location information, composite magnetic field strength at the magnetic sensor(s) (e.g., at least a composite threshold strength, a composite strength within a predetermined range, etc.), composite magnetic field direction at the magnetic sensor(s), detected light wavelengths, patterns, directions, intensities, and the like may be used as part of the information necessary to authenticate the module/footwear combination (e.g., to determine whether the article of footwear and the module are authorized for operation with one another). Combinations of different types of authentication systems also may be used without departing from this invention.

Additional aspects of this invention relate to methods for activating electronic modules (e.g., for collecting physical or physiological data, e.g., during exercise, workouts, or athletic performances, or for other functions or purposes) that include authenticating steps and/or the use of authenticating systems. Such methods may include, for example: (a) engaging a module with a module securing element provided in or on an article of footwear, wherein the module includes an electronic device (e.g., a sensing element that senses at least one physical or physiological characteristic associated with use of the article of footwear); (b) sensing whether the module and the article of footwear are authorized for operation with one another; and (c) activating the module or at least a first function of the module when the module and the article of footwear are determined to be authorized for operation with one another. Of course, the modules and/or at least some functions of the modules (e.g., the electronic device or portions or functions thereof) may be turned off, left off, deactivated, disabled, remain deactivated, remain disabled, etc., when the module and article of footwear are found to be unauthorized for use with one another and/or when the module is disengaged from the module securing element. Various ways of providing the authentication information may be used, e.g., including the use of one or more magnets and magnetic sensors, relative magnet/sensor positioning and orientation, magnetic field strength, magnetic field direction, one or more light sources and sensors, light patterns, light intensity, light wavelength, etc., as described above, without departing from this aspect of the invention.

C. Algorithm Selection Features

The interaction between the module and its activation system may be used for other purposes as well. For example, in accordance with at least some example aspects of the invention, features relating to the interaction between the module and its activation system may be used to provide information as to what data processing algorithm should be used, for example, to process data sensed, collected, and/or generated by the sensor(s) included with the module. Footwear systems in accordance with at least some of these example aspects of the invention may include: (a) an article of footwear including a module securing element; (b) a module activation system, wherein at least a portion of the module activation system is included with the article of footwear; and (c) a module removably engaged with the module securing element, wherein the module includes an electronic device (e.g., a sensing element that senses at least one physical or physiological characteristic associated with use of the article of footwear), and wherein an interaction between the module activation system and the module provides data processing algorithm selection information to the module.

Various ways of changing or controlling the interaction between the module and the module activation system may be used without departing from this invention. For example, if the module activation system includes a magnetic based sensor system, aspects of the interaction between the module and the module activation system may be changed or controlled, for example, by changing the orientation, position, location, magnetic field orientation, and/or pole orientation of one or more magnets with respect to the magnetic sensor element(s); by changing the strength of one or more of the magnets; etc. Different orientations, positions, locations, magnetic field orientations pole orientations, strengths, composite magnetic field strengths, composite magnetic field orientations, and the like may be sensed by systems and methods in accordance with examples of this invention and used as information to control and/or select the data processing algorithm used when the data is collected. Of course, light sources and light sensors (or other detection systems) may be used and various different characteristics regarding the detected light (or other parameter) may be used to control and/or select a data processing algorithm for use. Combinations of various different sensors and/or sensed parameters also may be used without departing from this invention.

As even more specific examples, different orientations, positions, locations, magnetic field orientations, magnetic pole orientations, magnetic strengths, composite magnetic field strengths, composite magnetic field orientations, light positions, light wavelength, transmitted/reflected lights and/or patterns, light intensity, and the like may be sensed by systems and methods in accordance with examples of this invention and used to indicate, for example, the type of footwear with which the module is engaged, a location on an article of footwear at which the module is engaged, etc. Then, once the type of footwear or location on the footwear information is determined, the module may be controlled (e.g., by a micro-processor) to initiate a specific type of data processing algorithm associated with the indicated type of footwear or location on the footwear.

As still more specific examples, each article of footwear produced by a specific manufacturer may include a magnet or light source (or other activation system element) as part of the module activation system, and different sensors included with the module may be activated, different data algorithms may be run, and/or different information may be presented to the user depending on the type of shoes to which the module is engaged. For running shoes, this magnet may be arranged with the north pole up or a light of wavelength A may be included in the shoe, and when this pole orientation or light wavelength is sensed by the appropriate sensor included with the module, the module may be controlled to collect GPS based speed, distance, and altitude information and to provide this information to the user's display. On the other hand, for golf shoes, this same manufacturer may arrange the magnet to always be south pole up or to use a different wavelength light source. Therefore, when this pole orientation or light wavelength is sensed by the sensor included with the module, the module may be controlled to generate only pedometer-based speed and/or distance information and provide this information to the user's display. A wide variety of different sensing elements and algorithms may be activated for use with a wide variety of different shoes (e.g., running shoes, cycling shoes, skateboarding shoes, walking shoes, golf shoes, basketball shoes, footwear used for electronic, video, or other games, etc.) without departing from this invention.

As additional more specific examples, an article of footwear produced by a specific manufacturer may include plural module securing elements (e.g., one at the back heel, one on the tongue, one on the lateral side, one on the medial side, one on the upper member, one at the toe area, and/or etc.). Different magnet arrangements (or light sources or other activation system elements) may be associated with each of these different module securing elements so as to enable the sensor to determine the location on the shoe where the module is mounted (e.g., two magnets at the heel area, north pole up at the upper area, south pole up at the tongue area, a light source at the toe area, etc.). Optionally, each module securing element may have its own independent, associated magnets or other module activation systems, or alternatively, if desired, portions of one activation system may be shared by more than one module securing element (e.g., by varying distance, direction, intensity to the various module securing element locations, etc.). Different sensors may be activated in the module, different data algorithms may be run, and/or different information may be presented to the user depending on which module securing element is sensed as being utilized by the user.

Examples of this aspect of the invention also relate to methods for selecting data processing algorithms for activation, e.g., using systems with data algorithm selection information capabilities like those described above. Such methods may include, for example: (a) engaging a module with a module securing element provided in or on an article of footwear, wherein the module includes an electronic device (e.g., a sensing element that senses at least one physical or physiological characteristic associated with use of the article of footwear); (b) determining a location in an article of footwear or a type of article of footwear with which the module has been engaged; and (c) selecting and/or initiating a data processing algorithm based on the determined location or type of article of footwear. As described above, features of a module activation system and/or its interaction with the module may be used to provide the footwear type or module location information in such methods, such as magnet or light source orientation, magnet or light source position, magnet or light source location, magnetic pole orientation, magnet or light strength or intensity, etc.

D. Data Input Features

Still additional aspects of this invention relate to data input features for electronic modules, such as modules associated with physical or physiological performance monitoring systems, e.g., for use with articles of footwear. Such systems may include, for example: (a) a housing; (b) a sensing element or other electronic module provided at least partially within or on the housing, e.g., for sensing information indicative of at least one physical or physiological characteristic associated with an athletic performance (e.g., speed and/or distance information, GPS information, altitude information, jump height information, user physical or physiological information, midsole compression information, etc.); and (c) a data input system provided at least partially within or on the housing for receiving input data in a wireless manner. Optionally, the housing (and its associated elements) may be engaged with an article of footwear (optionally, readily removably engaged with the article of footwear). The data input system may be capable of receiving input data at least at times when the electronic module is not performing other functions, such as when a sensing element is not sensing the physical or physiological characteristics associated with the athletic performance (e.g., at a point of sale location, at a race or event registration location, while mounted in an article of footwear, etc.). The data input system, in accordance with at least some examples of this invention, may utilize the sensing element to receiving input data.

The data input system may receive input data in various ways without departing from the invention. In accordance with at least some examples of this invention, the data input system may receive input data, at least in part, in a wireless manner, for example, via electromagnetic pulses, via light pulses, etc. Such data input systems may be provided, for example, in any of the various footwear systems and methods described above.

Still additional examples of this aspect of the invention relate to data handling methods, optionally using data input systems, e.g., like those described above. Such methods may include, for example: (a) providing a sensing element or other electronic device in or on a module (e.g., if desired, the sensing element or other electronic device may sense at least one physical or physiological characteristic associated with an athletic performance or perform other desired functions); and (b) inputting data into a memory provided in the module, wherein the inputting takes place in a wireless manner. The inputting may take place, for example, at least while the sensing element is not sensing the physical or physiological characteristics associated with the athletic performance (e.g., at a point of sale location, at a race or event registration location, while mounted in an article of footwear, etc.). In at least some examples of this invention, the sensing element may be used for receiving the input data. Examples of methods in accordance with this aspect of the invention further may include engaging the module with an article of footwear (optionally in a readily removable manner). The data inputting may take place prior to engaging the module with the article of footwear, after the module has been engaged with the article of footwear at least one time, while the module is engaged with the article of footwear, and/or at any other desired time. The data also may be input via electromagnetic or light pulses, as described above.

E. Footwear Aspects

Still additional aspects of this invention relate to footwear structures and methods for producing such footwear structures for use in systems and methods like those described above. Footwear structures in accordance with at least some examples of this invention may include: (a) an upper member; (b) a sole member engaged with the upper member; (c) a first module securing element included with at least one of the upper member or the sole member, wherein the first module securing element includes structure for removably engaging a module that includes at least one electronic device (e.g., a sensor for sensing at least one physical or physiological characteristic associated with use of the article of footwear); and (d) an interaction system included with at least one of the upper member or the sole member, wherein the interaction system interacts with a module when a module is present in the first module securing element. Portions of the interaction system may be included in either or both of the upper member and/or the sole member. In accordance with at least some examples of this invention, at least a portion of the interaction system may be provided so as to be located proximate to the module securing element at least when the article of footwear is in use.

The interaction system provided in the article of footwear may include a magnet and/or a magnetic sensor, as described above. Of course, a wide variety of other activation systems may be used without departing from the invention, such as a light or other radiation source, a light or radiation detector, a pressure producing element, a pressure sensor, etc. In at least some examples of the invention, the interaction system will induce a change in a measured parameter and/or otherwise induce an interaction or change in some property that may be detected by a sensor included with the module when the module is mounted at the module securing element.

Additionally, as described above, an article of footwear may include plural module securing elements and/or plural interaction systems without departing from the invention. As examples, an individual article of footwear may include multiple module securing elements, for example, in one or more of the following locations on both the upper and/or the sole member: rear heel, lateral heel, medial heel, lateral arch, medial arch, lateral toe, and medial toe. Additionally or alternatively, the instep area, the tongue member, and/or footwear securing system (e.g., laces, straps, buckles, etc.) may include one or more module securing elements and/or module interaction systems without departing from the invention. If desired, each individual module securing element may have a separate interaction system, multiple module securing elements may share a single interaction system and/or a portion thereof, and/or all module securing elements on an individual article of footwear may share a single interaction system, etc., without departing from this invention.

Methods in accordance with this example aspect of the invention include methods for producing an article of footwear. Such methods may include, for example: (a) engaging an upper member with a sole member; (b) providing a first module securing element in or on at least one of the upper member or the sole member, wherein the first module securing element includes structure for removably engaging a module with the article of footwear; and (c) providing a first interaction system in or on at least one of the upper member or the sole member, wherein the first interaction system operates, at least in part, to induce a change detectable at a module when a module is engaged with the first module securing element. Additional module securing elements and/or interaction systems may be provided, if desired, as described above.

II. SPECIFIC EXAMPLES OF THE INVENTION

While aspects of the invention generally have been described above, the following provides more detailed, specific examples of systems and methods in accordance with the invention. Those skilled in the art should understand, of course, that the following description constitutes descriptions of examples of the invention and should not be construed as limiting the invention in any way.

As described above, FIG. 1 generally illustrates an example of the invention and an example environment of use in which articles of footwear 100 (such as athletic footwear) are equipped with performance measuring or other electronic modules 102. The modules 102 may include detectors or sensing devices for sensing or collecting information during a performance (e.g., during exercise, an athletic event, or other performance activity). The modules 102 or the articles of footwear 100 further may include processing capabilities and/or transmission capabilities to provide information to the footwear user 104. While any desired type(s) of information may be sensed and/or provided to the user, more specific examples of the types of information include: user traveling speed information; distance traveled information; GPS information; altitude information; jump height information, user physical or physiological information (e.g., pulse, heart rate, body temperature, etc.); information derived from the GPS, speed, distance, or other information (e.g., warning information, route information, geographical information, etc.); midsole compression information; and the like. As further examples, rather than sensors, the electronic modules 102 may perform any desired function, such as transmission and/or reception of RFID, radio, audio, video, or other data or information. The data or information may be presented to the user via a display device 108, such as a watch, a PDA type device, a cellular telephone, an MP3 or other audio player, a head worn display device, a pager type device, etc. Alternatively or additionally, if desired, the sensed information may be used to change or control features of the footwear itself (e.g., to control the impact attenuation characteristics of the footwear) or to change or control other devices, with or without providing the information to a user 104.

Figure 2:
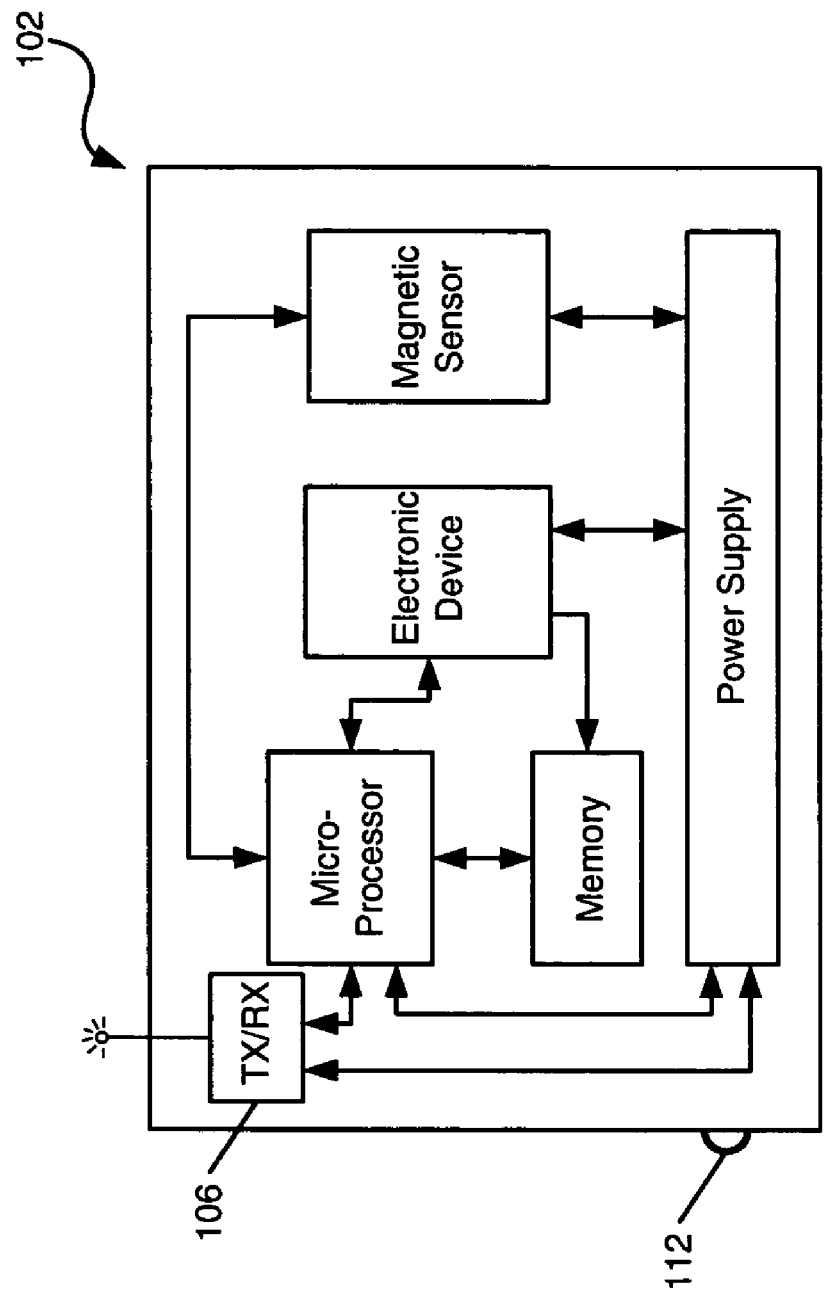
FIG. 2 illustrates a schematic block diagram of an example electronic module that may be used, e.g., for sensing physical or physiological characteristics or data associated with physical exertion or exercise or the like, in accordance with at least some examples of this invention.

FIG. 2 schematically illustrates example elements that may be included in a module 102 for use in an article of footwear, as shown in FIG. 1. FIG. 2 generally shows that a module 102 may include a power supply, which may constitute a battery (e.g., a rechargeable battery, etc.), a solar cell, and/or another type of power supply. The power supply supplies power for operating other elements that may be included in the module 102, such as a magnetic sensor element that, as will be described in more detail below, may be used as part of an activation or authentication system in at least some examples of systems and methods in accordance with this invention. Of course, as noted above, other types of activation and authentication systems may be used without departing from this invention, such as light sources/sensors, piezoelectric elements, etc.

The magnetic sensor may provide signal information to a microprocessor device, e.g., information indicating one or more characteristics of a magnetic field sensed by the magnetic sensor, such as magnetic field strength, magnetic field direction, magnet location, magnet polar orientation, number of magnet sources, positioning of magnetic sources, etc. When used as part of an authentication system, or even when used as part of an activation system, the microprocessor may process the incoming data from the magnetic sensor, determine whether the module 102 is located in an article of footwear and/or at a position or orientation suitable or authorized for use, and selectively operate an electronic device (e.g., a sensing device, etc.) when appropriate to do so (e.g., turn on the electronic device, enable its operation, and/or activate it when the microprocessor determines that the module 102 is properly oriented and/or is authorized for use with the shoe to which it was attached and/or turn the electronic device off, disable its operation, and/or deactivate it when the microprocessor determines that the module 102 is not properly oriented for use and/or is not authorized for use with the shoe to which it was attached). The electronic device may sense and/or collect any desired type of information, such as physical or physiological data associated with use of the article of footwear, as noted above; may transmit or receive data, audio signals, radio signals, video signals, transmit RFID information or other data; etc. Optionally, in at least some example systems, the magnetic sensor also may function as a physical and/or physiological data sensing device, without departing from the invention (e.g., used as a Hall sensor element). One or more LEDs 112 (or other indicator(s)) may be used to indicate when the module 102 is properly oriented, turned on, receiving data, shutting down, etc.

A memory may be provided for storing data, e.g., the data collected by the electronic device. The collected (and optionally stored) data optionally may be subjected to further processing in the microprocessor and/or sent to a peripheral display device as described above, e.g., via transmission elements 106 provided with the module 102. Of course, any desired type of data transmission mechanism and system may be used without departing from the invention, including wired and wireless connections. Additionally or alternatively, if desired, data from the electronic device, or even data further processed by the microprocessor, may be sent to a peripheral device where further processing takes place before information is displayed to the user (e.g., the display device 110 may operate in conjunction with a separate external processing system that further processes the data, optionally after combining it or using it with other external data or information, before displaying information to the user). Any suitable or desired processing may take place aboard the module 102, the display device 110, and/or any other desired processing device (not shown) without departing from this invention.

Of course, FIG. 2 merely shows examples of devices that may be included on a module 102 for engaging with a shoe. One or more of the elements shown in FIG. 2 may be included as part of the shoe structure rather than the module 102 without departing from the invention, such as the power supply, the memory, the microprocessor, the transmission system 106, at least portions of the magnetic sensor and/or the electronic devices, etc. When various elements are provided at locations other than the module 102, electrical connections and/or other communications with the module 102, if necessary, may take place in any desired manner, such as via wires, contact pads, contact pins, wireless connections, etc.

Figure 3A:
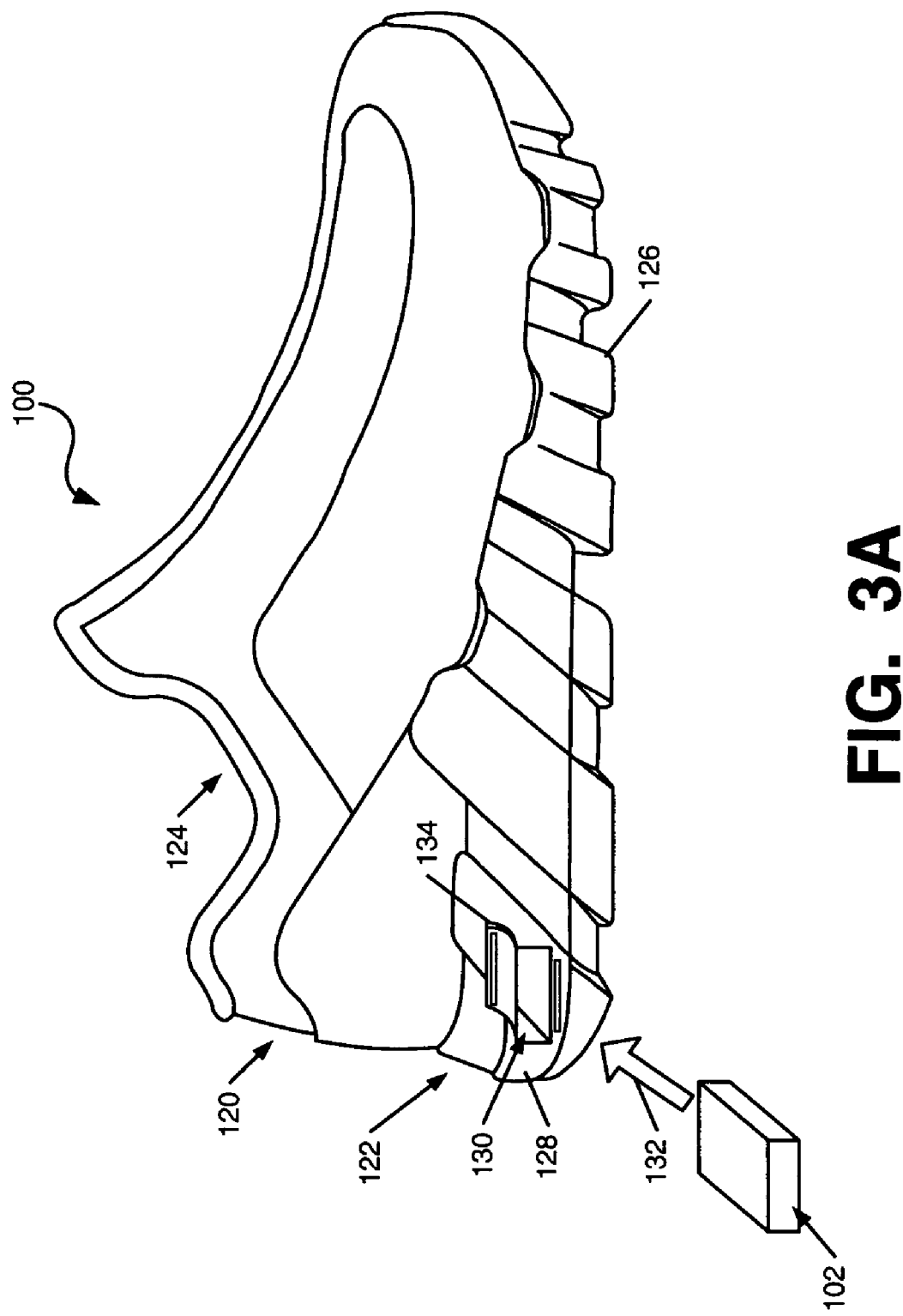
FIGS. 3A through 3C illustrate an example of a footwear system including an electronic module in accordance with some examples of this invention.
Figure 3B:
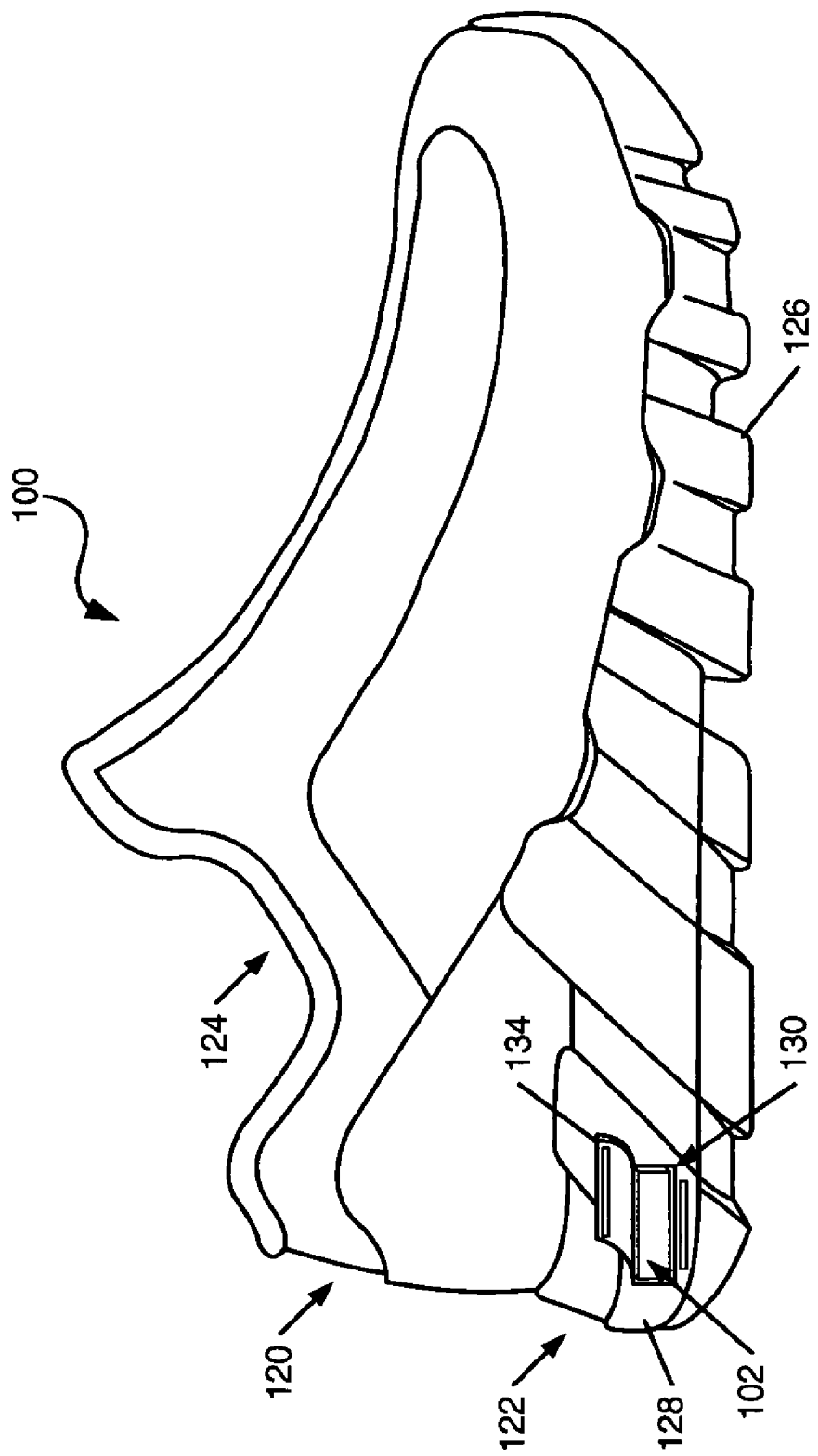
Figure 3C:
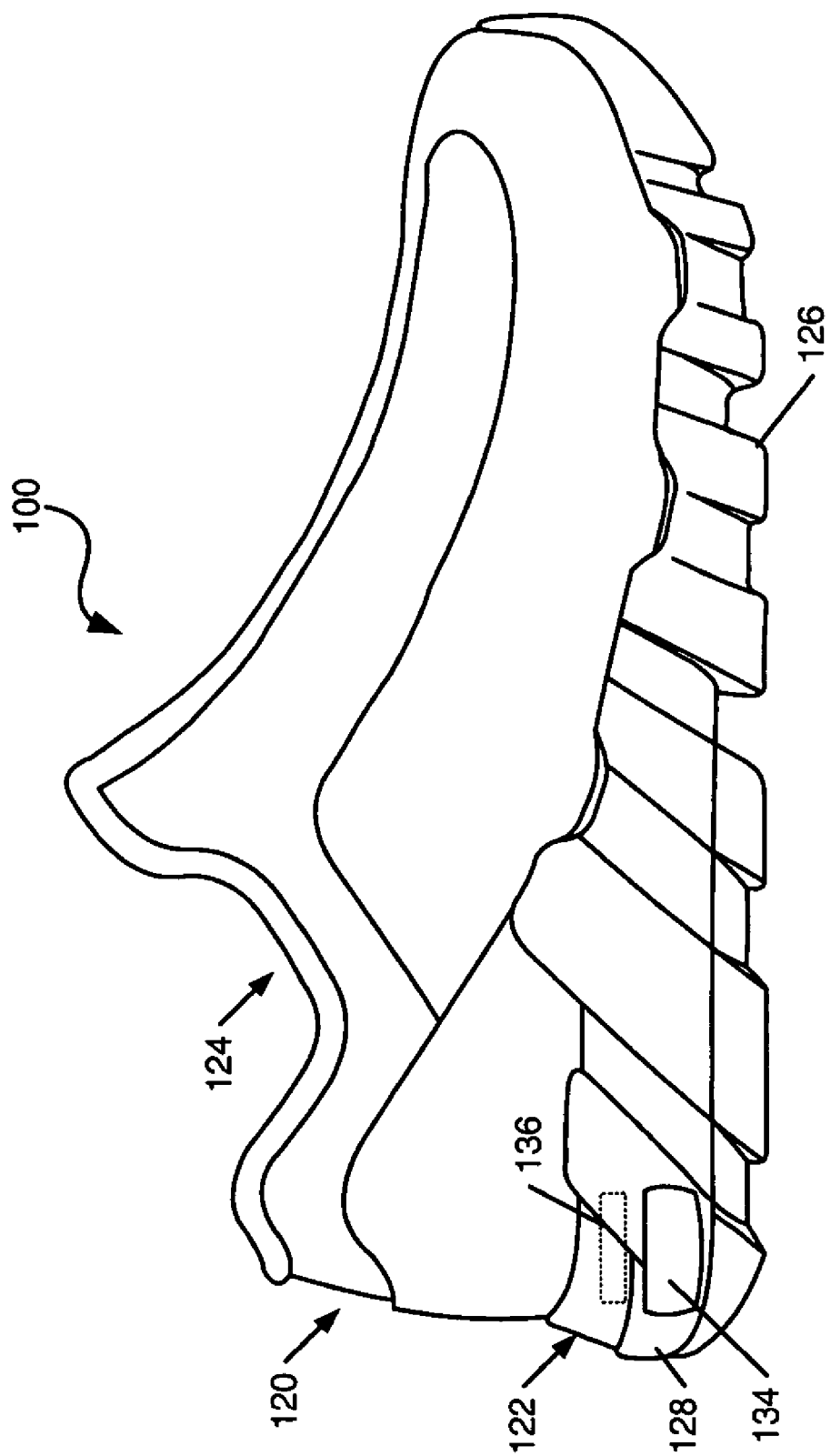

FIGS. 3A through 3C generally illustrate example steps involved in securing a module 102 to an article of footwear 100. As shown in FIG. 3A, as is conventional, an article of footwear 100 (e.g., athletic footwear or other footwear) may include an upper member 120 and a sole member 122 engaged with one another, e.g., in any conventional manner, such as via adhesives, cements, fusion or bonding techniques, mechanical connectors, sewing, stitching, and/or the like. The upper member 120 may include an opening 124 for receiving a foot, and a securing mechanism (not shown in FIGS. 3A through 3C), such as laces, straps, buckles, hook-and-loop fasteners, hook fasteners, magnetic fasteners, etc. The sole member 122 may include an outsole portion 126 (which typically contacts the ground in use), a midsole portion 128 (which typically may be used to attenuate impact reaction forces), and optionally, an insole portion (which typically engages the user's foot, not shown in these figures).

As shown in FIG. 3A, in this example structure 100, the midsole 128 has a module securing element 130 defined therein for receiving and securing a module including an electronic device, e.g., for measuring a physical or physiological characteristic associated with use of the article of footwear 100, e.g., a module 102 of the type illustrated in FIG. 2. While the module securing element 130 may take on many different sizes, shapes, and forms without departing from the invention, in this example structure 100, the module securing element 130 takes the form of a slot or opening defined in the midsole 128 into which the module 102 may be slid, as illustrated by arrow 132 in FIG. 3A.

Once inserted into the module securing element 130, as shown in FIG. 3B, the module 102 may be further secured to the article of footwear 100, if necessary. For example, as illustrated in FIGS. 3A and 3B, the opening 130 may include an associated cover or flap structure 134 that can be folded over to cover the opening 130 and thereby secure the module 102 in the opening 130 and to the article of footwear 100. While FIGS. 3A and 3B generally illustrate a hook-and-loop type fastener arrangement for holding the cover 134 in place over the opening 130, other fastener arrangements may be used without departing from the invention, such as snaps, buckles, hooks, and the like. Of course, other ways of securing the module 102 within the opening 130 and/or to the shoe 100 may be used without departing from the invention, such as retaining walls and elements, detents, threaded arrangements, spring loaded arrangements, mechanical connectors, adhesives, and the like. As still additional examples, if desired, structures may be provided in the opening 130 and/or on the module 102 to directly (and optionally releasably) attach these members to one another, such as in the manner in which memory cards are inserted into and attached within their respective slots (e.g., in digital cameras, etc.). Optionally, if desired, no cover member 134 is necessary, e.g., if other structures involved can adequately hold the module 102 in place, if protection of the module 102 from external debris and/or the elements is not an issue, etc. FIG. 3C illustrates the module 102 fully secured in the article of footwear 100 in this example structure (e.g., with the cover 134 over the opening 130 securing the module 102 therein).

FIG. 3C further illustrates example features of a footwear system that may be used to activate the module 102 and/or one or more functions of the module (e.g., to activate physical and/or physiological data collection, sensing, detection, etc.). Specifically, FIG. 3C illustrates that a portion of the footwear structure (the midsole 128 in this example structure) may include a magnet 136 therein. When the module 102 including the magnetic sensor (see FIG. 2) is inserted into the opening 130 in this example structure, the magnetic sensor will sense the magnetic field generated by the magnet 136, and the magnetic sensor then can send a signal to the microprocessor on board the module 102, which can further send a signal to activate various elements and/or functions of the module (e.g., activate a sensing device or other electronic module, activate the transmission/reception system 106, activate an RFID system, etc.).

As another specific example, if desired, the magnet 136 and the magnetic sensor may constitute a Hall sensor system, which can detect relative motion between the magnet 136 and the magnetic sensor on the module 102 (e.g., when the user's foot compresses the midsole member 128 during a step, jump, etc.). By detecting each compression of the midsole member 128 during a step, etc., the magnetic sensor/magnet system also can be used as at least part of the physical and/or physiological sensing device, e.g., to provide pedometer type speed and/or distance information, jump height sensing information, etc.). Relative motion between the magnetic sensor on the module 102 and the magnet 136 during insertion of the module 102 into the opening 130 also may be detected, e.g., to initially power on the module 102 and/or activate various functions of the module 102. In this manner, the module 102 can automatically be powered on immediately when it is inserted into the article of footwear 100 without the need for further action by the user and without the need for electrical contacts between the module 102 and the shoe 100. Alternatively, if desired, other steps may be involved in initially turning on the module 102 (e.g., user interaction with an ON/OFF switch, etc.).

The example structure 100 shown in FIGS. 3A through 3C has other potential useful functions. For example, the magnet 136 and the magnetic sensor also may be used as an automatic shut-off element. More specifically, if the magnetic sensor system does not detect motion for a predetermined period of time (e.g., no compression of the midsole 128 or other relative motion between the magnet 136 and the sensor on the module 102 for 5 minutes, or the like), the microprocessor on board the module 102 (or other location) may be programmed and adapted to send a signal to shut down various devices and/or elements on the module 102, e.g., to conserve battery life. Of course, other types of detecting systems may be used to determine whether use of the footwear is continuing, such as motion detectors, light detectors (e.g., interrupted or moving light beams, etc.), accelerometers, and the like. If desired, the microprocessor also may be programmed to automatically shut down the module 102 and/or at least some functions of the module 102 when the module 102 is removed from the opening 134, e.g., in response to signals generated by the magnetic sensor system or other detection system.

Figure 4:
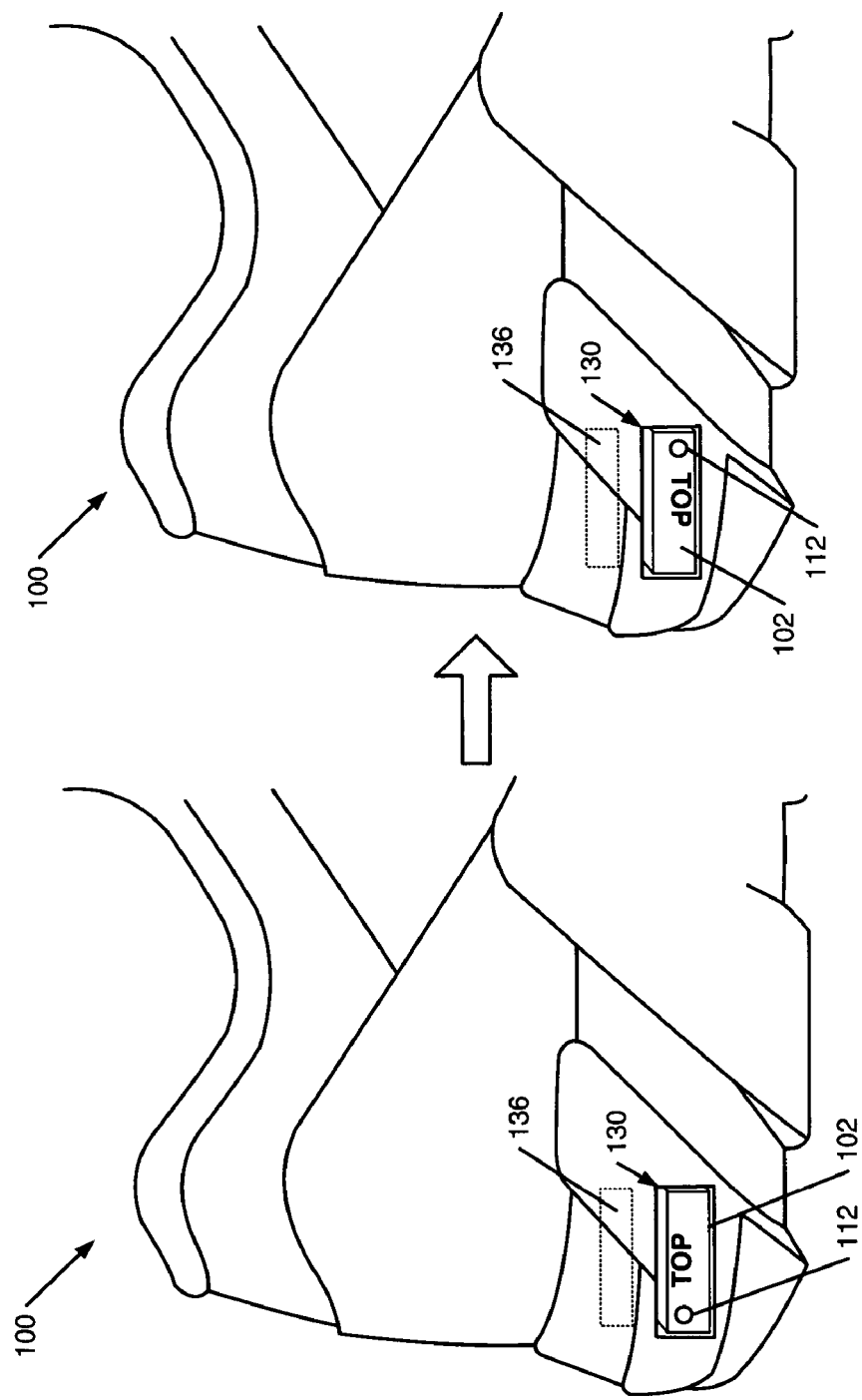
FIG. 4 illustrates an example ON/OFF feature for a footwear system including an electronic module in accordance with some examples of this invention.

Various ways of turning the module 102 and/or various functions of the module 102 on and off may be provided without departing from this invention. For example, as shown in FIG. 4, the module 102 may be designed such that it can be turned on and/or operated when oriented in the article of footwear in a first orientation (e.g., a "top up" orientation in this example, as shown at the left hand side of FIG. 4), e.g., using the Hall sensor system or other desired "on/off" switching mechanism as described above. However, if the user removes the module 102 from the opening 130 and reorients it in another manner not corresponding to its original "activation" orientation (a "top down" orientation in this illustrated example, as shown at the right hand side of FIG. 4), this may provide an indicator to the microprocessor that the module 102, or at least some functions thereof, are to be turned off or deactivated. Switching magnetic pole orientations (e.g., north pole up to south pole up, etc.) also may be used to indicate reorientation of the module 102 (e.g., if the magnet is on board the module 102, etc.). In response to such reorientations of the module 102, the microprocessor then can send suitable signals to shut down the module 102 or various functions thereof (e.g., the LED 112 may blink a few times to indicate that the module 102 is shutting down and then turn off when the shut down procedure is completed, etc.). This example feature gives users the ability to easily and selectively control the on/off functions of the module 102, e.g., to enable them to easily shut down the module 102 (or at least its transmission and/or reception capabilities or other capabilities) for airline travel, at hospitals, and/or at other locations where transmission and/or reception capabilities are banned or potentially dangerous, to save battery life, etc. Of course, other ways of reorienting the module 102 may be used without departing from the invention, such as turning it about a horizontal axis, placing it in another opening or module securing element, etc. This feature provides for easy and convenient ON/OFF switching and helps keep the user from losing the module 102 and/or running down its power supply when its use is not necessary or desired. Alternatively or additionally, if desired, other ways of switching the module 102 on and off may be used without departing from the invention, such as by including an ON/OFF switch, disconnecting the module 102 from its power supply (e.g., breaking electrical connections if the power supply is independent from the module 102 (such as included as part of the article of footwear, etc.), etc.

The various example footwear systems described above in connection with FIGS. 2-4 may be considered as including basic "authentication systems" because both the article of footwear 100 and the module 102 must have interacting elements and/or interact in some manner to activate the module 102 and/or at least some of the module's functions (e.g., the magnet 136 in the shoe 100 and the magnetic sensor in the module 102, or vice versa). Of course, more sophisticated "authentication systems" may be provided without departing from this invention. For example, if desired, the magnetic sensor on the module 102 may be used to detect additional information regarding the magnetic field output by the magnet 136, and the microprocessor on the module 102 may be programmed and adapted to activate the module 102 and/or various functions thereof if and only if the detected magnetic field information meets certain predetermined parameters. For example, if the magnetic sensor is capable of measuring or determining magnetic field strength, the microprocessor could be adapted to activate the module 102 and/or various functions of the module 102 if and only if the magnetic field strength meets a certain threshold level and/or if and only if the magnetic field strength falls within a certain range. In this manner, the module 102 could not be used with any type of shoe or any type of shoe with a simple magnet mounted therein, but rather only with shoes that have an activation or authenticating system that matches the authentication parameters set in the module's microprocessor. Of course a wide variety of other parameters may be measured and compared against threshold or predetermined authorized range values for activation and/or authentication purposes without departing from the invention, such as magnetic field orientation, magnetic field direction, magnetic pole orientation, numbers of magnets, distance between magnet(s) and the sensor, etc. Additionally or alternatively, other source and sensor combinations may be used without departing from the invention, such as light sources and light detectors, and the "authenticating" information may take the form of, for example, light direction, number of light sources, distance between light source and detector, light source wavelengths, a predetermined pattern of blocked and transmitted light (e.g., light blocked by the module and/or transmitted through the module, etc.), incident light angle, etc. Also, if desired, both the source and sensor (e.g., magnet, light, radiation, etc.) may be mounted on a single one of the module or the article of footwear, e.g., provided interaction between the module and the article of footwear may be used to change the sensed information (e.g., by blocking light, by transmitting light, by blocking magnetic fields, by changing magnetic fields, by splitting light beams, by changing light beam directions, etc.).

Optionally, if desired, the authentication information necessary to activate and/or enable use of a module 102 with a specific article of footwear may be set by the manufacturer at the factory, by retailers at a point of sale location, by consumers at home, and/or at any other suitable or desired location in the supply chain and/or during use of the footwear.

Figure 5:
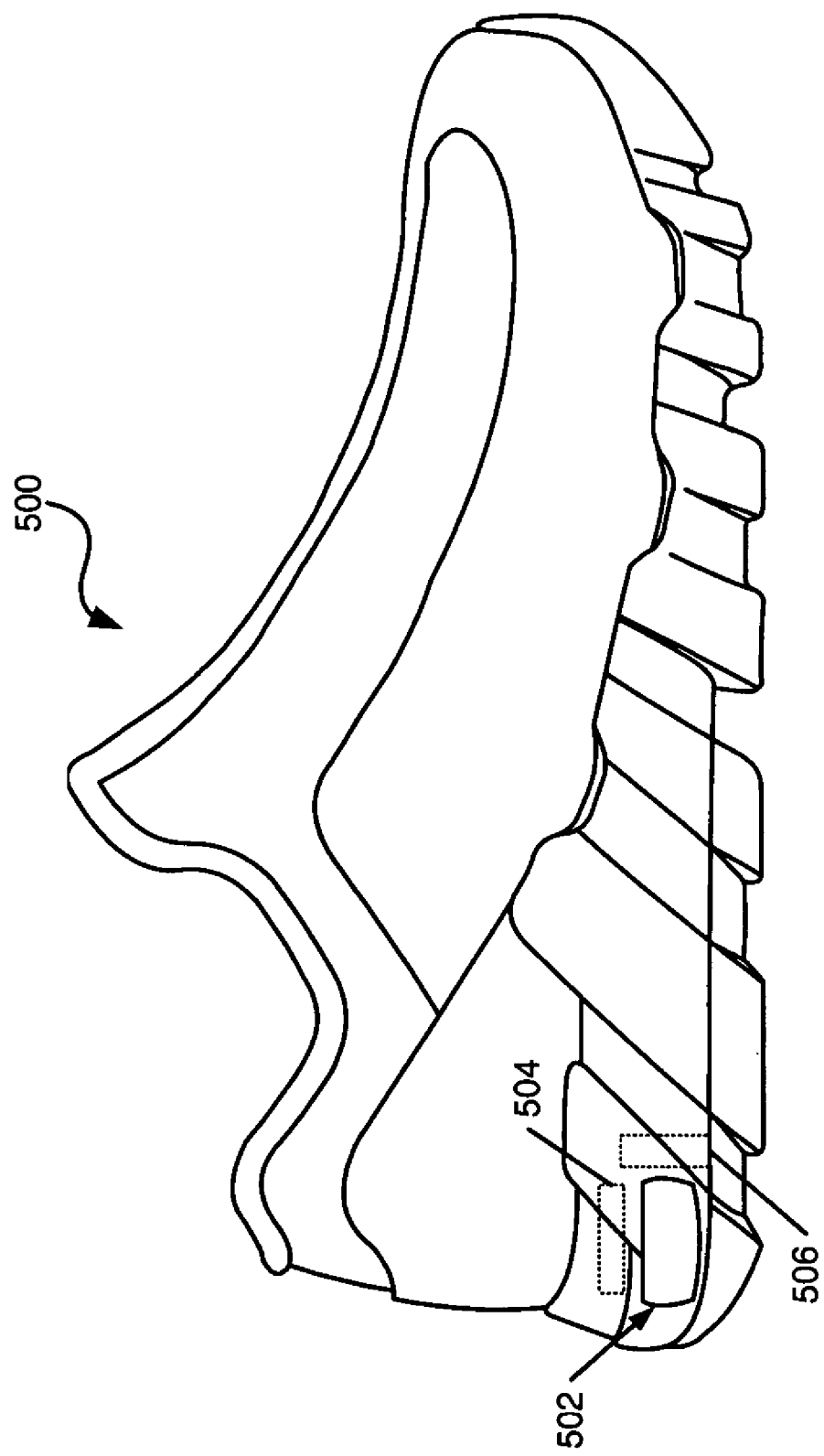
FIG. 5 illustrates additional examples of module activation/authentication features in accordance with some examples of this invention.

FIG. 5 illustrates an example article of footwear 500 with a module securing element 502 having a module mounted therein in the general manner described above in conjunction with FIGS. 3A through 3C (of course, any desired type of module securing element and module may be used without departing from the invention). In this example structure 500, two magnets 504 and 506 are arranged around the module securing element 502, and these magnets 504 and 506 may be used in the manner described above for activating the module (e.g., an electronic device or sensing element included with the module), for maintaining the module in an active state while in use, etc. The use of two (or more) magnets 504 and 506 as shown in FIG. 5 also can affect and increase the information available for authentication purposes, including, for example, composite magnetic strength measured at the magnetic sensor, composite magnetic field direction measured at the magnetic sensor, the magnets' pole orientation(s), the number of magnets, magnet position(s) relative to the sensor, magnet positions relative to one another, and the like. Again, the microprocessor included with the module (or at another appropriate location) can limit activation of the module (e.g., performance sensing elements (e.g., physical or physiological sensing characteristics associated with the physical performance and/or use of the footwear) or other electronic devices included in the module) to times when the module is located in a module securing element having magnets or other authenticating elements (e.g., light or other radiation sources, etc.) meeting predetermined thresholds, parameters or characteristics.

Also, if desired, different types of sensors and various different types of sensors in combination may be used for authentication purposes without departing from the invention, such as a combination of a magnetic source and sensor element with a light source and sensor element, optionally with either or both of the sources having one or more characteristics that fall within a predetermined range or meet a predetermined threshold for authentication purposes. As can be readily understood from the above description, any number of sensors and any combination of types of different sensors may be used for authentication purposes without departing from this invention.

FIG. 6 illustrates additional example features that may be included in systems and methods in accordance with at least some examples of this invention. FIG. 6 shows a footwear system 600 that includes an article of footwear 602 and at least one module 102, e.g., for measuring physical or physiological characteristics associated with use of the article of footwear 602 and/or the activities performed while wearing the article of footwear 602. In this example structure 600, the article of footwear 602 includes three independent module securing elements 606(*a*), 606(*b*), and 606(*c*), one (606(*a*)) located in the heel area of the sole member 608 of the article of footwear 602 as generally described above, one (606(*b*)) provided as a pocket element defined in or on the upper member 610 of the article of footwear 602, and one (606(*c*)) provided in the instep area (e.g., as a pocket member defined in the shoe's tongue, etc.). Separate activation/authentication systems 610(*a*), 610(*b*), and 610(*c*) are provided in this example structure 600 for each module securing element 606(*a*), 606(*b*), and 606(*c*), respectively. In this illustrated example, the activation/authentication systems 610(*a*), 610(*b*), and 610(*c*) take the form of magnets. However, as described above, various different types of activation systems and/or authentication systems may be provided, and various different parameters may be measured and used for authentication and activation purposes without departing from this invention.

Of course, if desired, a single activation/authentication system may be provided for use with all of the module securing elements on a given article of footwear without departing from this invention. As still another alternative, if desired, two or more module securing elements on a single article of footwear may share at least some portions of a single activation/authentication system (e.g., share a magnet, a light source, etc.) without departing from this invention.

The example footwear system 600 of FIG. 6 also helps illustrate another potential feature that may be available in accordance with at least some examples of this invention. More specifically, by providing different types of and/or characteristics for the individual activation/authentication systems provided on an article of footwear 602, the microprocessor (optionally on board the module 102) can determine, based on the signals generated by the activation/authentication system, where the module 102 is located on the article of footwear 602. For example, magnet 610(*a*) associated with module securing element 606(*a*) may have a first strength, pole orientation, or other orientation feature with respect to the module 102 (and/or the magnetic sensor on board the module 102), while magnet 610(*b*) associated with module securing element 606(*b*) may have a different strength, pole orientation, or other orientation feature with respect to the module 102, and magnet 610(*c*) associated with module securing element 606(*c*) may have yet a different strength, pole orientation, or other orientation feature with respect to the module 102. If the magnetic sensor (or other activation/authentication system element) provides this data to the microprocessor, the microprocessor can use this information to determine the specific module securing element (e.g., 606(*a*), 606(*b*), or 606(*c*) in this example) at which the module 102 is located. As a still further option, if desired, the microprocessor can activate specific types of sensors and/or otherwise activate, initiate, or utilize a specific type of data processing algorithm based on the determined module 102 location (e.g., module securing location 606(*a*), 606(*b*), or 606(*c*)) within the article of footwear 602.

Some more specific examples follow. For example, the article of footwear 602 and/or module 102 may be designed and programmed such that the module 102 was designed to be placed in the heel based module securing element 606(*a*) for use during long distance running or jogging. This module 102 placement information (e.g., which may be determined based on detected magnetic strength, pole orientation, light beam interruption, light beam wavelength, etc.) may be used by the microprocessor, for example, to activate a GPS based sensor element and/or a data processing algorithm to provide GPS-based speed, distance, elapsed time, altitude, and/or other desired information to the user (e.g., via wireless transmission to a display device as described above in conjunction with FIG. 1). On the other hand, the article of footwear 602 and/or module 102 may be designed and programmed such that the module 102 is placed in the upper based module securing element 606(b) for use during walking or similar type exercise (e.g., when playing golf, walking along the beach, walking on a treadmill, etc.), and this placement information (e.g., based on magnetic strength, pole orientation, light beam interruption, light beam wavelength, etc.) may be used by the microprocessor, for example, to activate a pedometer based speed and distance monitoring systems and/or a data processing algorithm to provide pedometer based speed and distance information to the user (e.g., via wireless transmission to a display device as described above in conjunction with FIG. 1). As another example, the article of footwear 602 and/or module 102 may be designed and programmed such that the module 102 is placed in the instep or tongue based module securing element 606(c) for use in playing basketball, and this placement information (e.g., based on magnetic strength, pole orientation, light beam interruption, light beam wavelength, etc.) may be used by the microprocessor, for example, to activate jump height sensors, speed sensors, accelerometers, etc., and/or to activate data processing algorithms to sense this type of data and/or send it to the user (e.g., via wireless transmission, etc.).

Optionally, if desired, a user could use the article of footwear 600 with multiple modules 102 simultaneously mounted in the multiple module securing elements (e.g., 606(a), 606(b), etc.) without departing from the invention. In such a situation, the physical and/or physiological data or other data produced by the sensing device or other electronic devices associated with the modules 102 may be displayed to the user on one or more display devices in any desired manner, e.g., on individual display devices dedicated to each module 102, on a single display device according to a predetermined algorithm (e.g., in a repeated, changing manner), on a single display device based on user demand, etc. Alternatively, if desired, a footwear system 600 may be designed so as to permit operation of only one module 102 at a given time.

Figure 7B:
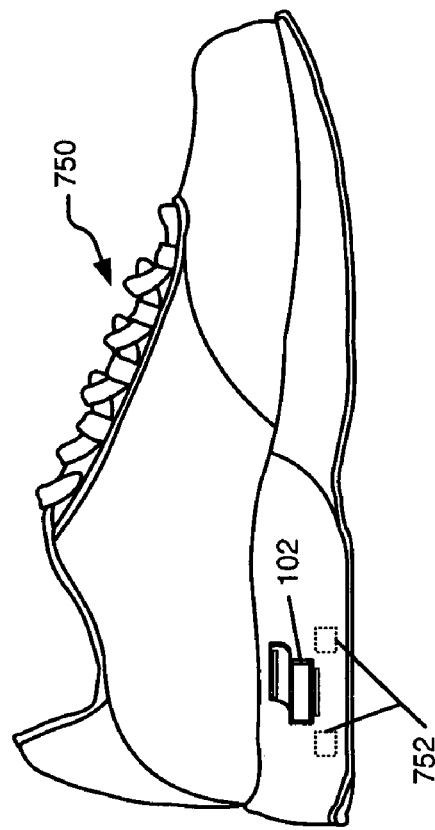
FIGS. 7A and 7B illustrate examples of module activation/authentication features, footwear type or module securing element location determination features, and/or data algorithm selection features that may be used in accordance with some examples of this invention.
Figure 7A:
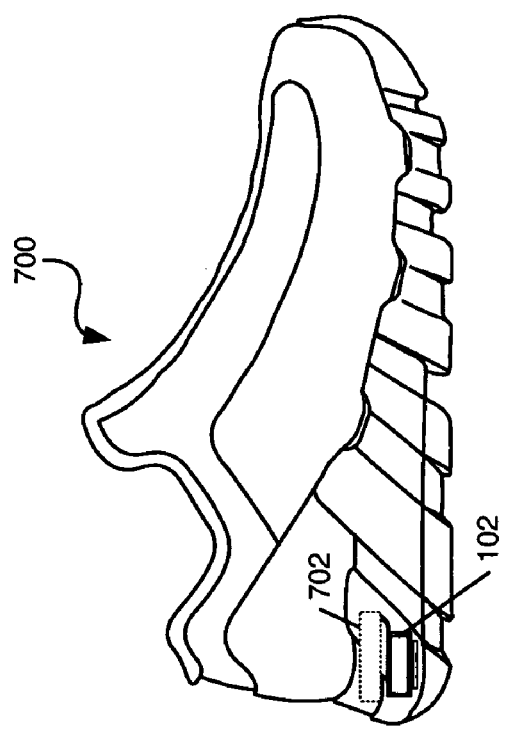

The above principles of selective electronic device activation and/or data processing algorithm selection may be extended to situations involving different types of footwear. FIGS. 7A and 7B illustrate an example. A footwear manufacturer may design one type of shoe with one type of activation/authentication characteristics and another type of shoe with different activation/authentication characteristics. As more specific examples, a footwear manufacturer may produce all of its running or jogging shoes 700 to have an activation/authentication system with a single magnet 702 (or other activation system) having one strength (as shown in FIG. 7A) and all golf or walking shoes 750 to have an activation/authentication system with plural magnets 752 (or other activation system) having a different composite strength (as shown in FIG. 7B). A third type of shoe (e.g., basketball shoes) may have yet a third independent set of magnetic or other characteristics. Of course, any of the various example characteristics described above may be used for activation and/or authentication purposes and/or for distinguishing one module securing element location from another without departing from the invention (e.g., magnetic field orientation, magnetic pole orientation, magnet location relative to the sensor, number of magnets, magnet locations relative to one another, light wavelength, light intensity, number of light sources, light transmission/reflection/blocking properties, light beam splitting properties, incident light angle, etc.). In this manner, simply by placing a module 102 within a shoe, the sensor on board the module 102 (or other appropriate location) can detect the activation/authentication information and characteristics, it can feed the information to the microprocessor, and the microprocessor associated with the module 102 can determine the type of footwear (e.g., 700 or 750 in the illustrated example) in which the module 102 is mounted. The type of footwear information also can be used by the microprocessor to determine which sensors or other electronic devices to activate and/or otherwise determine which data processing algorithm to run, e.g., in the manner described above in conjunction with FIG. 6 (e.g., collecting and displaying GPS based information for use with running shoes v. collecting and displaying pedometer based information for golf or walking shoes v. collecting and displaying jump height information for basketball shoes, v. collecting and displaying cycling oriented information, v. running an algorithm, collecting, and displaying information for gaming purposes (e.g., electronic games, video games, games involving physical activities, etc.), etc.

Figure 8:
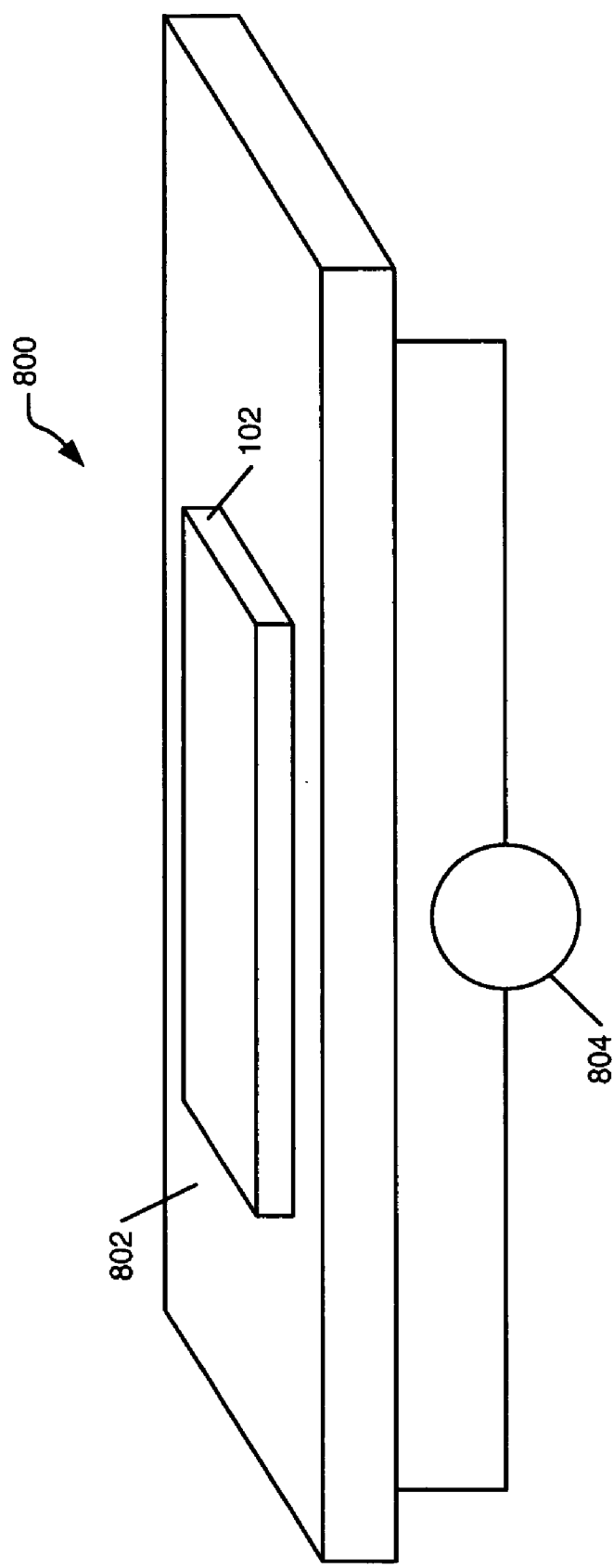
FIGS. 8 and 9 illustrate examples of various module data input features that may be provided and used in accordance with at least some examples of this invention.

The module 102 as described above also may receive input data without departing from this invention (e.g., via a conventional wired or wireless connection, through the transmitter/receiving mechanism 106, if any, etc.). For example, the module 102 may receive information indicating the activating and/or sensing characteristics for which it is authorized for use, owner information, track or route information, etc. If desired, the magnetic sensor, light sensor, or other device on board the module 102 used for receiving input for activation and/or authentication purposes also may be used for receiving input data (e.g., for storage in the microprocessor, a memory on board the module 102, an external memory, etc.). FIG. 8 illustrates an example system 800 for inputting data into a module 102 (e.g., to its microprocessor registers, an on board memory, etc.). The system 800 includes an electromagnet 802 and a device 804 that causes the electromagnet 802 to pulse on and off (or otherwise send pulsed signals, e.g., a coiled wire and an AC current source may be used, etc.). The electromagnetic pulses (controlled by device 804) may be used to activate the magnetic sensor on board the module 102 (see FIG. 2), which causes it to generate an output (as described above in connection with the example activation and authentication procedures). By controlling the pulses (e.g., no pulse=a logical 0 bit, a pulse=a logical 1 bit), input data can be generated and stored in the microprocessor, a memory, or other device on board the module. This feature could be used, for example, at a point of sale location (e.g., to input purchaser's identification information, activation/authentication information, and/or other desired information), at a race venue (e.g., to input the athlete's identification information, track or route information, etc.), at another point of use location (e.g., a gym, a spa, etc.), or the like. Of course, any desired data may be input in this manner, and any type of input source information may be used (e.g., a pulsed light source and detector rather than magnetic source/sensor, etc.), etc., without departing from the invention.

Figure 9:
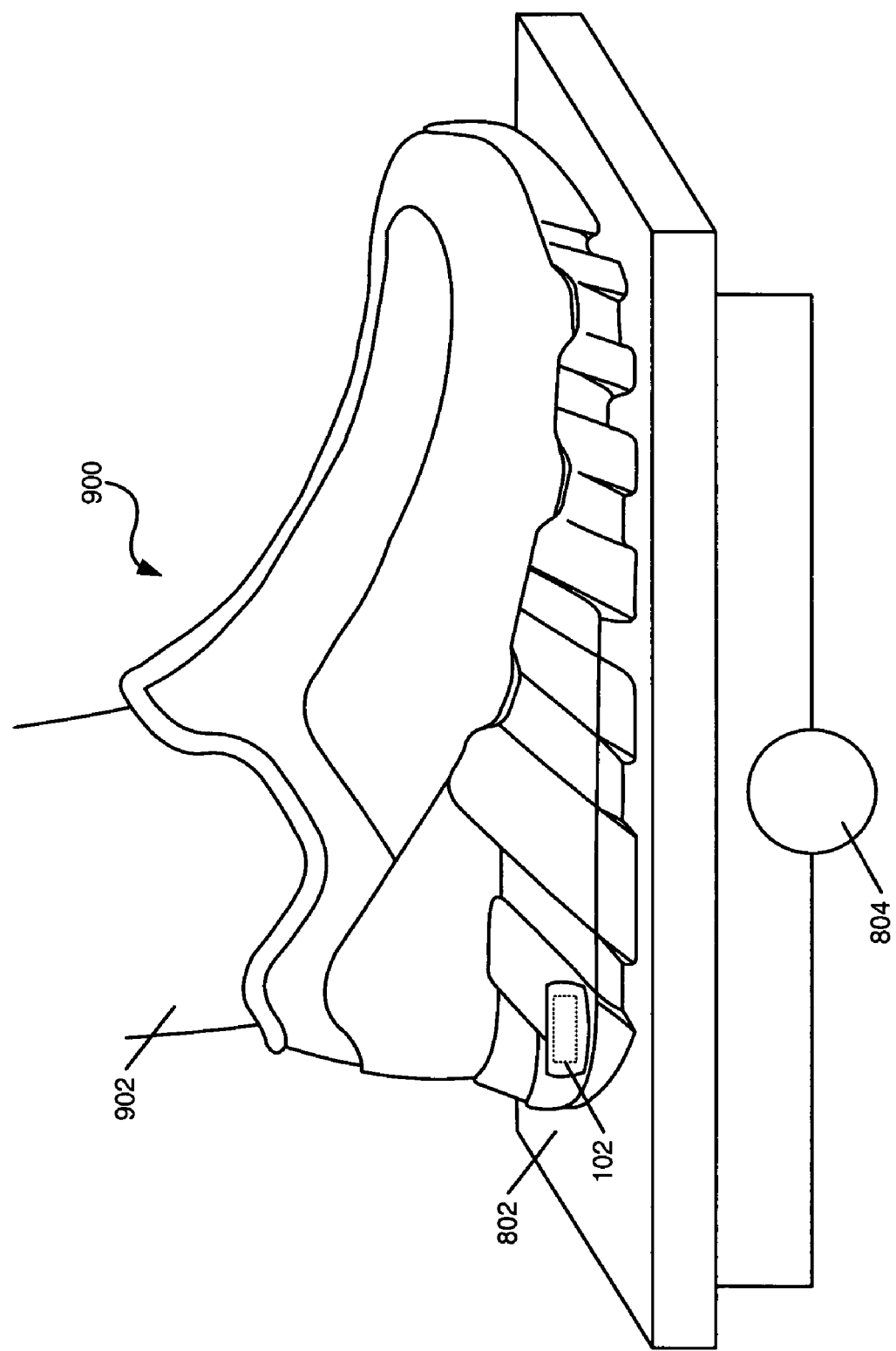

Moreover, as illustrated in FIG. 9, the module 102 need not be removed from the article of footwear when receiving input data. Rather, as shown in FIG. 9, the module 102 may be engaged with an article of footwear 900 and still receive input data in the manner described above in conjunction with FIG. 8. In fact, the article of footwear 900 may be actually secured to the foot of a user 902 at the time input data is transmitted via electromagnet 802 (or other input data source, such as a pulsed light source, etc.). Such systems may be particularly useful for inputting data and/or initiating some function of the module, for example, at race venues or other point of use locations.

The data input systems and methods described above in conjunction with FIGS. 8 and 9 allows one to use an external pulsed magnet, light source, or other source to input data into the module 102. One advantage of this arrangement is that the data input system is contact free, does not use radio or IR input, and is simple to use. Also, it enables the module to be produced in a watertight, sealed manner, if desired.

Data input in this manner may be used for a wide variety of purposes. One example enables users (or others) to set various "modes" of operation. As one example, rather than actually inputting data into a memory, the frequency of the incoming signal may be detected and used to set various modes of operation (e.g., a 10 Hz input places the module 102 in a "test" mode, 20 Hz places it in a "silent" or unactivated mode, 60 Hz places it in full operation mode (e.g., including FM data transmission to the display device, etc.). etc. The "test mode" may be used, for example, at the factory, by placing the module in a test jig and testing its function(s) (e.g., running a predetermined battery of tests thereon, running diagnostics, etc.). At retail stores or other point of sales locations, the module 102 may be placed on an electromagnet as shown in FIG. 8 or 9 and given data input (e.g., a specific predetermined frequency) to activate it for first time use once purchased (e.g., to zero out any mileage logged on the module and/or footwear from previous in-store try-ons, etc.). At athletic events, the shoe wearer could stand on an electromagnet mat (or other appropriate data input device) and input data could be used to place the module in a special "rewards mode" (e.g., prompting it to send out data indicating total mileage ran, total miles on the shoes, total miles over a time period, etc., and the wearer could check her progress against previously designated goals and win prizes or rewards based on the logged mileage data, etc.). These methods of data input also may be used to place the module in various predetermined or special operational modes, such as pedometer mode, run mode, basketball jump height recording mode, game modes, etc, e.g., for specific uses.

Of course, a wide variety of different modes and uses may be utilized based on input introduced, for example, by the systems and methods described in conjunction with FIGS. 8 and 9. As more specific examples, such systems and methods may be used: (a) to activate an "airline sleep mode" (e.g., to turn off the data transmission and/or reception capabilities, e.g., at a kiosk or other location in airports, etc., to turn off the module for predetermined time periods, etc.); (b) to place the module in a "game mode" to collect data used for video games, physical exercise games, or other games or reward programs, etc.; (c) to upgrade or add new firmware or software; (d) to activate a "power save mode," e.g., for shipping or other non-use time periods (e.g., very low power to save shelf life, etc.); (e) to reset the system (e.g., mileage counters, game scores, etc.); (f) to signal the module to output total mileage, identification information, other desired information, etc.; (g) to input personal information (e.g., name, address, height, weight, running club, identification information, etc.); etc. One also could use data input systems like those shown in FIGS. 8 and/or 9, for example, for the following: (a) to provide "low power" or "anti-dead" operational override (to allow users to use up every bit of battery life and still obtain the stored information); (b) to set up "partner codes" at the manufacturer (e.g., to set the authentication parameters for use with the module, etc.); (c) to change the security keys used for data scrambling and encryption (if desired or used by the system); (d) to set performance limits (e.g., to indicate that the module typically will be used at slow speeds, etc.), which may be used to enable the module's detectors to work better at the slower end of a speed continuum and not optimize its settings for use at fast speeds or over a wide range of speeds; (e) to change receiver (e.g., radio, video, MP3 player, other display device) performance characteristics to match the user's model(s); (f) to change output or display change frequency (e.g., update or change the displayed information twice a second, once every ten seconds, etc.); (g) to change operational/power consumption modes (e.g., higher power to provide very high accuracy step counts or other data v. lower power, which may miss a few steps or data points (e.g., suitable when just walking around) but saves battery life; etc. A wide range of other input also may be provided to the module 102, e.g., via the systems shown in FIGS. 8 and 9, without departing from this invention.

Many of the examples above describe interactions between a device mounted on an article of footwear and a device included with a module for activation/authentication purposes. The invention is not limited, however, to use in this specific environment or structural arrangement. Rather, if desired, both the source and the sensor may be included on only one member (e.g., both on the module or both on the article of footwear) and changes in the detected parameters when the module is inserted in the article of footwear (or otherwise interacts with the article of footwear) may be used for activation/authentication purposes. For example, changes in the detected magnetic field, light beam interruption, changes in light beam transmission/reflection/angle/intensity, physical interactions, and the like may be induced when a module is inserted into an article of footwear, and such changes may be used for activation/authentication purposes without departing from the invention.

Also, much of the description above relates to systems in which a magnet or other source is located on the shoe and is used for activation and/or authentication purposes. This is not a requirement in all examples of the invention. For example, if desired, the magnet or other activation/authentication initiator source may be provided on another device, such as on a watch, ring, bracelet, clothing, a peripheral device, and the like, and then this other device may be moved near the module in the shoe to initiate data collection (e.g., for activation and/or authentication purposes).

Additionally, much of the description and specific examples above relate to systems and methods in which the electronic module mounted in the article of footwear provides or senses information relating to the use of the article of footwear (e.g., physical or physiological data associated with use of the article of footwear). Systems and methods according to at least some examples of the invention are not limited to these types of uses. Rather, if desired, the electronic devices or modules may perform any desired function and/or sense or monitor any type of data without departing from this invention. Additional examples of potential functions or operations include, but are not limited to: data transmission and/or reception functions, enabling. RFID transmission and/or reception functions, controlling other systems (e.g., an active impact-attenuation control system, etc.), controlling a radio or other audio/video transmission or display device, etc.

III. CONCLUSION

While the invention has been described with respect to specific examples including presently preferred modes of carrying out the invention, those skilled in the art will appreciate that there are numerous variations and permutations of the above described systems and methods. For example various aspects of the invention may be used in different combinations and various different subcombinations of aspects of the invention may be used together in a single system or method without departing from the invention. Also, various method steps described above may be changed, changed in order, omitted, and/or additional steps may be added without departing from this invention. Thus, the invention should be construed broadly as set forth in the appended claims.

I claim:

1. A footwear system, comprising:
an article of footwear having a module securing element;
a module removably engaged with the module securing element, wherein the module includes an electronic device; and
an authentication system configured to electronically sense a signal when the module is engaged with the module securing element and process the signal to determine whether the article of footwear and the module are authorized for operation with one another.

2. A footwear system according to claim 1, wherein the authentication system senses whether the module is engaged with the module securing element in a first orientation.

3. A footwear system according to claim 2, wherein the authentication system further enables activation of the module or at least a first function of the module when the module is engaged with the module securing element in the first orientation.

4. A footwear system according to claim 2, wherein the authentication system does not enable activation of the module or at least a first function of the module when the module is engaged with the module securing element in any orientation other than the first orientation.

5. A footwear system according to claim 1, wherein the authentication system does not enable operation of the module or at least a first function of the module when the module is determined to be not authorized for operation with the article of footwear.

6. A footwear system according to claim 1, wherein a first portion of the authentication system is included with the article of footwear and a second portion of the authentication system is included with the module.

7. A footwear system according to claim 1, wherein the authentication system includes a magnetic sensor system.

8. A footwear system according to claim 7, wherein a first portion of the magnetic sensor system is included with the article of footwear and a second portion of the magnetic sensor system is included with the module.

9. A footwear system according to claim 1, wherein the authentication system includes at least a first magnet.

10. A footwear system according to claim 9, wherein the authentication system senses whether the article of footwear and the module are authorized for operation with one another, at least in part, by sensing whether the first magnet is oriented in a predetermined manner with respect to the module in the module securing element.

11. A footwear system according to claim 9, wherein the authentication system senses whether the article of footwear and the module are authorized for operation with one another, at least in part, by sensing whether the first magnet is oriented at a predetermined location with respect to the module in the module securing element.

12. A footwear system according to claim 1, wherein the authentication system includes plural magnets.

13. A footwear system according to claim 12, wherein the authentication system senses whether the article of footwear and the module are authorized for operation with one another, at least in part, by sensing whether the plural magnets are arranged in a predetermined manner.

14. A footwear system according to claim 12, wherein the authentication system senses whether the article of footwear and the module are authorized for operation with one another, at least in part, by sensing whether the plural magnets are arranged at predetermined locations with respect to one another or with respect to the module.

15. A footwear system according to claim 1, wherein the module senses at least speed or distance information.

16. A footwear system according to claim 1, wherein the authentication system further includes a module activation system that activates the module or at least a first function of the module when the authentication system determines that the article of footwear and the module are authorized for operation with one another.

17. A footwear system according to claim 16, wherein interaction between the module activation system and the module provides data processing algorithm selection information to the module.

18. A footwear system according to claim 17, wherein the interaction between the module activation system and the module indicates a location on the article of footwear at which the module is engaged, and the module initiates a data processing algorithm associated with the indicated location in response to the interaction.

19. A footwear system according to claim 18, wherein the module activation system includes a magnet and the module includes a magnetic sensor.

20. A footwear system according to claim 19, wherein the location on the article of footwear is indicated, at least in part, based on a strength of the magnet as measured by the magnetic sensor.

21. A footwear system according to claim 19, wherein the location on the article of footwear is indicated, at least in part, based on an orientation of the magnet with respect to the magnetic sensor.

22. A footwear system according to claim 19, wherein the location on the article of footwear is indicated, at least in part, based on a position of the magnet with respect to the magnetic sensor.

23. A footwear system according to claim 18, wherein the module activation system includes plural magnets and the module includes at least one magnetic sensor.

24. A footwear system according to claim 23, wherein the location on the article of footwear is indicated, at least in part, based on a composite strength of the magnets as measured by the magnetic sensor or sensors.

25. A footwear system according to claim 17, wherein the article of footwear includes multiple module securing elements, and the interaction between the module activation system and the module indicates a specific module securing element among the multiple module securing elements at which the module is engaged, and the module initiates a data processing algorithm associated with the indicated specific module securing element in response to the interaction.

26. A footwear system according to claim 25, wherein each module securing element includes an independent module activation system portion.

27. A footwear system according to claim 26, wherein each independent module activation system portion includes a magnet and the module includes a magnetic sensor.

28. A footwear system according to claim 27, wherein a specific module securing element with which the module is engaged is indicated, at least in part, based on a strength of the magnet as measured by the magnetic sensor when the module is engaged with the specific module securing element.

29. A footwear system according to claim 27, wherein a specific module securing element with which the module is engaged is indicated, at least in part, based on an orientation of the magnet with respect to the magnetic sensor when the module is engaged with the specific module securing element.

30. A footwear system according to claim 27, wherein a specific module securing element with which the module is engaged is indicated, at least in part, based on a position of the magnet with respect to the magnetic sensor when the module is engaged with the specific module securing element.

31. A footwear system according to claim 25, wherein each module securing element includes a pocket for receiving the module.

* * * * *